US010845312B2

(12) United States Patent
Vinogradova et al.

(10) Patent No.: US 10,845,312 B2
(45) Date of Patent: Nov. 24, 2020

(54) LABEL-FREE DETECTION OF SIALIC ACID USING SURFACE-ENHANCED RAMAN SCATTERING MICROSCOPY

(71) Applicants: Ekaterina Vinogradova, San Antonio, TX (US); Hugo Navarro-Contreras, San Antonio, TX (US); Miguel Jose-Yacaman, San Antonio, TX (US)

(72) Inventors: Ekaterina Vinogradova, San Antonio, TX (US); Hugo Navarro-Contreras, San Antonio, TX (US); Miguel Jose-Yacaman, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/746,360

(22) PCT Filed: Jul. 22, 2016

(86) PCT No.: PCT/US2016/043578
§ 371 (c)(1),
(2) Date: Jan. 19, 2018

(87) PCT Pub. No.: WO2017/015568
PCT Pub. Date: Jan. 26, 2017

(65) Prior Publication Data
US 2018/0238805 A1 Aug. 23, 2018

Related U.S. Application Data

(60) Provisional application No. 62/195,787, filed on Jul. 22, 2015.

(51) Int. Cl.
*G01N 21/65* (2006.01)
*B22F 1/00* (2006.01)
(Continued)

(52) U.S. Cl.
CPC ......... *G01N 21/658* (2013.01); *A61B 5/0075* (2013.01); *B22F 1/0018* (2013.01);
(Continued)

(58) Field of Classification Search
CPC .................................................. G01N 21/658
See application file for complete search history.

(56) References Cited

U.S. PATENT DOCUMENTS 5,296,346 A * 3/1994 Katopodis ............. G01N 33/52
435/18
2007/0154903 A1* 7/2007 Marla ...................... B82Y 5/00
435/5

(Continued)

OTHER PUBLICATIONS

Konstantin V. Sokolov, "Detection of Sialic Acid Residues and Studies of Their Organization in Normal and Tumor c I-Acid Glycoproteins as Probed by Surface-Enhanced Raman Spectroscopy", 1993, Applied Spectroscopy.*

(Continued)

*Primary Examiner* — Maurice C Smith
(74) *Attorney, Agent, or Firm* — Norton Rose Fulbright US LLP

(57) ABSTRACT

Certain embodiments are directed to systems and methods using surface enhanced Raman scattering (SERS) detection. More specifically, the present invention describes a system and method of use for SERS detection of sialic (N-acetylneuraminic acid) using citrate-reduced silver nanoparticles.

5 Claims, 12 Drawing Sheets

(51) Int. Cl.
    *A61B 5/00*    (2006.01)
    *G01N 33/52*   (2006.01)
    *G01N 33/574*  (2006.01)
    *B22F 9/24*    (2006.01)
    *A61B 5/08*    (2006.01)
    *A61B 5/145*   (2006.01)

(52) U.S. Cl.
    CPC ..... *G01N 33/523* (2013.01); *G01N 33/57415* (2013.01); *A61B 5/08* (2013.01); *A61B 5/14546* (2013.01); *A61B 5/4312* (2013.01); *A61B 5/4504* (2013.01); *B22F 9/24* (2013.01); *B22F 2999/00* (2013.01)

(56) References Cited

U.S. PATENT DOCUMENTS

| | | | |
|---|---|---|---|
| 2008/0268450 A1* | 10/2008 | Nam | C12Q 1/6804 435/6.11 |
| 2009/0068108 A1 | 3/2009 | Sokolov et al. | |
| 2009/0311798 A1* | 12/2009 | Wimberger-Friedl | C12Q 1/6827 436/171 |
| 2012/0058471 A1* | 3/2012 | Graham | C12Q 1/6823 435/6.11 |
| 2015/0017258 A1 | 1/2015 | Azzazy et al. | |

OTHER PUBLICATIONS

N. Stefenelli, "Serum Sialic Acid in Malignant Tumors, Bacterial Infections, and Chronic Liver Diseases" 1985, Cancer Research Clinical Oncology (Year: 1985).*

Kemal Erbil, "Use and Limitations of Serum Total and Lipid-Bound Sialic Acid Concentrations as Markers for Colorectal Cancer" (Year: 1985).*

Maria J. Marin, "Glyconanoparticles for the plasmonic detection and discrimination between human and avian influenza virus†", Biomol. Chem., 2013 (Year: 2013).*

Ozturk, Leyla Koc, "Salivary Total Sialic Acid Levels Increase in Breast Cancer Patients A Preliminary Study", 2011,Bentham Science Publishers (Year: 2011).*

Yuan-Ting, "Label-free in-situ monitoring of protein tyrosinenitration in blood by surface-enhanced Raman spectroscopy", 2015 (Year: 2015).*

Xiao X. Han, "Surface-enhanced Raman scattering for protein detection" 2009 (Year: 2009).*

International Search Report and Written Opinion Issued in Corresponding PCT Application No. PCT/US2016/43578, dated Oct. 19, 2016.

International Preliminary Report on Patentability Issued in Corresponding PCT Application No. PCT/US2016/43578, dated Feb. 1, 2018.

Vinogradova, et al., "Surface-enhanced Raman Scattering of N-Acetylneuraminic Acid on Silver Nanparticle Surface," Journal of Raman Spectroscopy, 45(9), 2014.

* cited by examiner

LABEL-FREE DETECTION OF SIALIC ACID USING SURFACE-ENHANCED RAMAN SCATTERING MICROSCOPY

This application is a national phase application under 35 U.S.C. § 371 of International Application No. PCT/US2016/043578, filed Jul. 22, 2016, which claims priority to U.S. Provisional Patent Application Ser. No. 62/195,787 filed Jul. 22, 2015. Both applications are incorporated herewith in their entirety.

BACKGROUND

The present invention generally relates to a system and method of using surface enhanced Raman scattering for detection of sialic acid levels in subjects with cancer.

Breast cancer is the leading cancer type among women and its early detection is a challenge. Several techniques are used to diagnose breast cancer. The leading technique is mammography. The ability of a mammogram to detect breast cancer depends on the size of the tumor, the density of the breast tissue, and the skill of the radiologist administering and reading the mammogram. Mammography is less likely to reveal breast tumors in women younger than 40 years as compared to older women. This may be because younger women have denser breast tissue that appears white on a mammogram. Likewise, a tumor appears white on a mammogram, making it hard to detect. In addition, the use of X-Rays is not convenient for many subjects and can trigger unwanted effects. Other techniques for detecting breast cancer include ultrasound, magnetic resonance imaging (MRI) and pathological analysis of biopsies. There is a need for additional compositions and techniques to enhance early detection of cancers, particularly breast cancer.

SUMMARY

The current state-of-the-art is lacking in methods to efficiently and rapidly detect sialic acid. Currently available methods of measurement of SA can be broadly classified as colorimetric, fluorometric, enzymatic, and highly sensitive high performance liquid chromatographic (HPLC) procedures. The methods of specific detection and quantification (such as chromatographic method and Enzyme Linked Immunoadsorbent Assay, ELISA) are complicated, expensive, and time consuming, while the more robust techniques (for example, colorimetric assays) suffer from non-specificity and interference. In contrast, the method described herein offers the advantages of being highly sensitive, fast, and more economical in terms of cost and labor-effort approach than the above-mentioned techniques.

Certain embodiments include methods using surface-enhanced Raman scattering (SERS) for molecular recognition and analytical detection of sialic acid (SA), also known as N-acetylneuraminic acid (Neu5Ac).

One embodiment includes a method that allows for the surface-enhanced Raman scattering detection of sialic acid using citrate-reduced silver nanoparticles (cit-AgNPs). Certain aspects are directed to a detectable complex comprising sialic acid coupled to or complexed with a citrate-reduced silver nanoparticles (cit-AgNPs). In certain aspects, the detectable complex can be detected and/or measured using surface enhanced Raman scattering (SERS). The SERS method can be used to determine the presence, qualitatively and/or quantitatively, of negatively charged biological or chemical molecules of interest in a sample, without the need for design of complimentary binding agents. The SERS-based method can be used for rapid detection of a target analyte at a very low concentration ($10^{-7}$ M) in small probe volumes (10 μL). In certain aspects the target analyte can be detected at concentrations ranging from at least or about $10^{-3}$, $10^{-2}$, $10^{-4}$, $10^{-5}$, 10-, to $10^{-7}$M including all values and ranges there between. In further aspects the analytes are measured in volumes of at least, at most, or about 5, 10, 15, or 20 μL, including all values and ranges there between.

In certain aspects SERS spectra of SA are recorded for unmodified citrate-reduced silver nanocolloids. Density functional theory (DFT) calculations have been used to support the spectroscopic data and provide a reliable vibrational assignment. The results show the bonding affinity of SA molecules for cit-AgNPs, which can offer a label-free probe for the analytical detection of this monosaccharide in various media.

Certain embodiments include methods of detecting an analyte, such as SA (e.g., Neu5Ac), in a liquid sample, comprising: mixing a sample containing an analyte or an analyte with cit-AgNPs followed by a drop coating deposition process and measurement of a SERS spectrum. The spectral fingerprint and increased signal intensity allow for identification of the target analyte.

In one embodiment the method begins with the preparation of the silver nanoparticle suspension via reduction of $AgNO_3$ by sodium citrate according to the Turkevich method (24). A solution of silver nitrate in deionized water was heated to about 95° C., and a solution of trisodium citrate is added. About 15 min later, the color of the solution turns grayish yellow, indicating the formation of nanoparticles (AgNPs). The solution is cooled to room temperature and the AgNPs are washed by centrifugation-redispersion cycles with deionized water three times and stored in the dark until used. For the SERS measurements, an aliquot (e.g., 10 μl) of an aqueous solution of an analyte (e.g., SA) were added to an equal volume of silver colloid ($1.4\times10^{-4}$ M), the resulting mixture was then deposited onto a quartz slide and dried at room temperature. The drop coating deposition drying process leads to the formation of a ring-like structure along the edge part of the drop, caused by the "coffee ring effect". This specific drying process together with higher affinity of SA for silver than citrate promote binding of SA onto the SERS-active AgNPs surface as well as concentrating it in the ring, allowing detection down to the limit of $10^{-7}$ M with a laser power of 25 mW in approximately 10 minutes (exposure time of 2 s). In some embodiments the molarity of the reactants (silver nitrate and trisodium citrate) and/or the temperature are varied. A solution of silver nitrate and deionized water can be heated to 90, 100, 110, 120, or 130° C., including all values and ranges there between. The molarities of the silver nitrate and the trisodium citrate reactants can vary from 0.025, 0.05, 0.25, 0.5, 1.0, 1.5, 1.75, 2.0, 2.25, to 2.5 mM, including all values and ranges there between. These parameters can be altered to increase the homogeneity of the silver nanoparticles.

The methodologies described herein have applications related to the detection of biological and chemical analytes. In certain aspects methods can be used as a research tool for designing experimental conditions suitable for detection of anionic species by SERS.

Increased sialic acid levels have been shown to be a characteristic feature in saliva of breast cancer patients (6), therefore aspects of the methods can be used as a diagnostic tool to detect and monitor sialic acid in body fluids (such as saliva and blood) of breast cancer patients. The high sensitivity of sialic acid as a tumor marker has been reported in several cancerous conditions (such as lung cancer), consequently aspects of the described methods can be used to detect these cancerous conditions and monitor cancer patients during the treatment.

It has been reported that total serum sialic acid levels increased in primary osteoarthritis, in certain aspects method described herein can be used to detect non-cancer-related inflammatory conditions as well.

In certain embodiments, saliva can be used as a diagnostic fluid, which would be simple, non-invasive, and safe. The ability to diagnose cancer such as breast cancer in its early stages and follow the progression of patients during treatment is vital to significantly decreasing morbidity and mortality rates in affected females, as well as reducing costs of treatment. A saliva sample can be pretreated using a plurality of methods known in the art in order to be analyzed. In certain aspects the sample can be treated or processed using dilution, extraction, centrifugation, filtration, and/or precipitation to remove unwanted, undesired, or irrelevant sample components and/or concentrate or purify the target analyte.

As an example, a saliva sample is first diluted with equal volume of DI water and vortexed vigorously to reduce the viscosity of the saliva. The resulting sample is then centrifuged at 10,000 rpm for 5 min to remove any unwanted particles (e.g. debris or cells). Finally, the SA contained in the supernatant for instance can be released in the presence of 2 M $CH_3COOH$ by means of microwave hydrolysis (only 10 min required) (23). In the case of the measurement of free SA, the hydrolysis step is not necessary and should be replaced by a protein precipitation technique.

Certain methods described herein can be used for a variety of applications including detecting SA in blood serum, saliva, and other bodily fluids or biological samples. Depending on the application a sample pretreatment method known in the art should be used in order to release sialic acid and avoid the presence of interfering substances in the sample.

The combination of ease of sample preparation and the high sensitivity of SERS has far reaching applications in the field of molecular recognition and analytical detection.

The disclosed system and method of use is generally described, with examples incorporated as particular embodiments of the invention and to demonstrate the practice and advantages thereof. It is understood that the examples are given by way of illustration and are not intended to limit the specification or the claims in any manner.

To facilitate the understanding of this invention, a number of terms may be defined. Terms defined herein have meanings as commonly understood by a person of ordinary skill in the areas relevant to the present invention.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Terms such as "a", "an", and "the" are not intended to refer to only a singular entity, but include the general class of which a specific example may be used for illustration. The terminology herein is used to describe specific embodiments of the invention, but their usage does not delimit the disclosed device or method, except as may be outlined in the claims. The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

It will be understood that particular embodiments described herein are shown by way of illustration and not as limitations of the invention. The principal features can be employed in various embodiments without departing from the scope of the invention. Those skilled in the art will recognize, or be able to ascertain using no more than routine experimentation, numerous equivalents to the specific device and method of use described herein. Such equivalents are considered to be within the scope of this invention and are covered by the claims.

All publications and patent applications mentioned in the specification are indicative of the level of those skilled in the art to which this invention pertains. All publications and patent application are herein incorporated by reference to the same extent as if each individual publication or patent application was specifically and individually indicated to be incorporated by reference.

The system and/or methods disclosed and claimed herein can be made and executed without undue experimentation in light of the present disclosure. While the system and methods of this invention have been described in terms of certain embodiments, it will be apparent to those skilled in the art that variations may be applied to the system and/or methods and in the steps or in the sequence of steps of the method described herein without departing from the concept, spirit, and scope of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 10A) main plot, intensities of the 1391 $cm^{-1}$ line; (FIG. 10B) intensities of the 1002 and 1237 $cm^{-1}$ lines.

DESCRIPTION

Figures 1A, 1B:
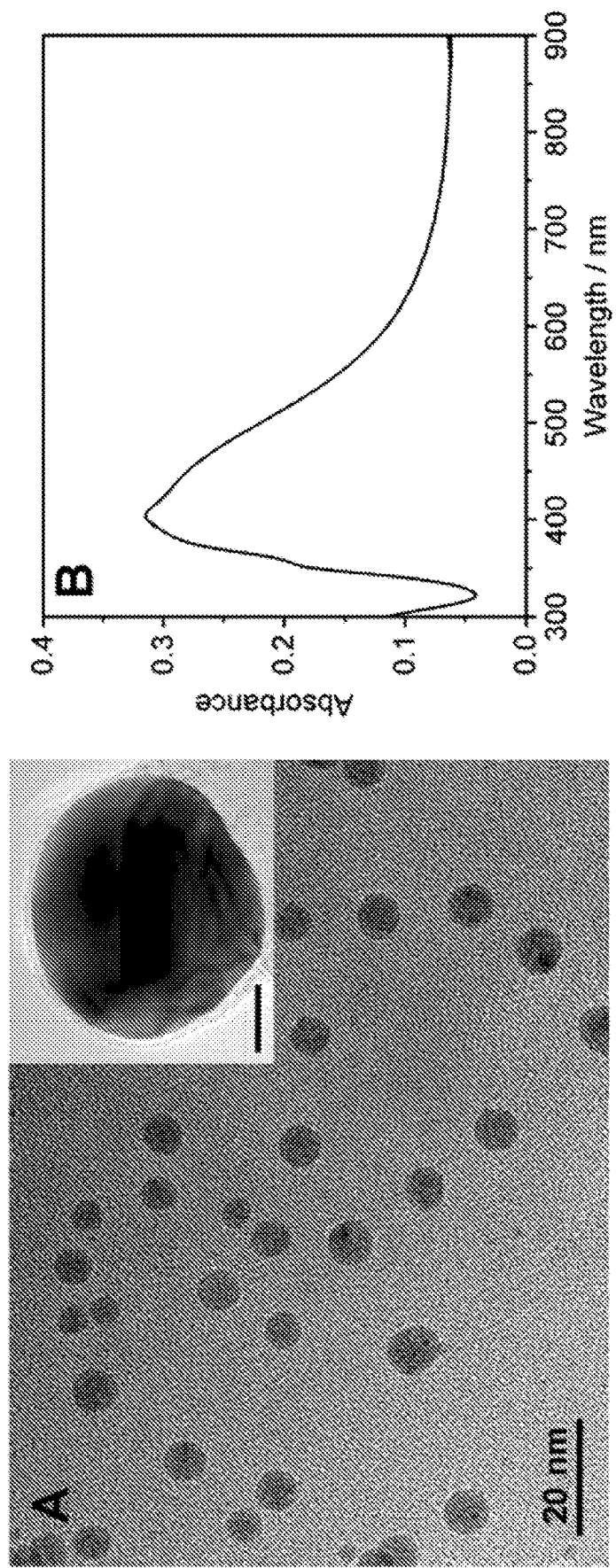
FIG. 1. TEM Transmission electron microscopy images of citrate-AgNPs: (A) faceted nanoparticles of 2-10 nm in diameter. The inset shows a high-resolution image of an individual nanoparticle; (B) Uv-Vis absorption spectrum of the silver colloid.

Embodiments of the invention are directed to a fast, reliable technique based on nanotechnology that can be used for cancer screening at very low cost and in a family doctor environment. If the test is positive will allow the patient to go to a specialist for further studies and follow up.

Oncologist suggested to classify a patient in two ways according the cancer stage which are named: 0, I, IIa, IIb, IIIa, IIIb, IIIc, and IV. The stages are defined as follows:

Stage 0 (noninvasive, carcinoma in situ) breast cancer—In stage 0, there is no evidence of cancer cells breaking out of the part of the breast in which they started, or of getting through to or invading neighboring normal tissue.

Stage I breast cancer—In stage I, the tumor measures up to two centimeters and no lymph nodes are involved.

Stage II (invasive) breast cancer—In stage II, the tumor measures between two to five centimeters, or the cancer has spread to the lymph nodes under the arm on the same side as the breast cancer.

Stage III (locally advanced) breast cancer—In stage III, the tumor in the breast is more than two inches in diameter across and the cancer is extensive in the underarm lymph nodes, or has spread to other lymph nodes or tissues near the breast.

Stage IV (metastatic) breast cancer—In stage IV, the cancer has spread beyond the breast, underarm and internal mammary lymph nodes to other parts of the body near to or distant from the breast.

According to the American Cancer Association the possibility of cancer remission is strongly dependant of the stage.

I. Surface Enhanced Raman Spectroscopy (SERS) of Sialic Acid

The Raman effect is well known and documented in Physics. It is the result of scattering of light that result in a transition to the first vibrational stage. When photons are scattered from an atom or molecule, most photons are elastically scattered (Rayleigh scattering), such that the scattered photons have the same energy (frequency and wavelength) as the incident photons. A small fraction of the scattered photons (approximately 1 in 10 million) are scattered by an excitation, with the scattered photons having a frequency different from, and usually lower than, that of the incident photons. That fraction is the Raman scattering.

In recent years a technique known as Surface Enhanced Raman Spectroscopy (SERS) has been developed. SERS results in a dramatic increase in the intensity of the Raman signal for adsorbates on particular surfaces, which occurs because of an enhancement in the electric field provided by the surface. When the incident light strikes the surface localized surface plasmons are excited. The field enhancement is greatest when the plasmon frequency, $\omega_p$, is in resonance with the radiation. Arrangements of nanoparticles are typically employed in SERS experiments as these surfaces provide an area on which these localized collective oscillations can occur.

Sialic acid can be used to detect cancer. Sialic acid-rich glycoproteins (sialoglycoproteins) bind selectin in humans and other organisms. Metastatic cancer cells often express a high density of sialic acid-rich glycoproteins. This overexpression of sialic acid on surfaces creates a negative charge on cell membranes. This creates repulsion between cells (cell opposition) and helps these late-stage cancer cells enter the blood stream.

Sialic acid (SA) is a family of 43 naturally occurring derivatives of the nine-carbon acidic monosaccharide neuraminic acid (5-amino-3,5-dideoxy-D-glycero-D-galacto-nonulsonic acid). N-acetylneuraminic acid (Neu5Ac) is the predominant form of sialic acid and almost the only form found in humans (1). An N-acetyl group and the carboxyl group confer a negative charge on the molecule under physiological conditions and characterize it as a strong organic acid (2). Sialic acids are present in all vertebrates as terminal components of oligosaccharide chains of mucins, glycoproteins, and glycolipids, and have been recognized to be involved in the regulation of a great variety of biological phenomena. In human beings they occur in body fluids (blood plasma, breast milk, synovial fluid, sweat, gallbladder excretions, gastric juices, and urine) and tissues (erythrocytes, leucocytes, platelets, salivary glands, throat, stomach, cervix, cartilage, colon, etc.) (3). Sialic acid concentrations in body fluids may reflect metabolic status and body tissue levels. For instance, elevated plasma sialic acid concentration is strongly related to the presence of microvascular complications in type I diabetes (4) and an increased risk for coronary heart disease (5).

Elevated SA levels have been shown to be a characteristic feature in saliva of breast cancer patients and, therefore, they have been suggested as a non-invasive predictive marker for patients with this type of cancer (6). Currently available methods of specific detection and quantification (such as chromatographic methods) are complicated, expensive, and time consuming, while the more robust techniques (for example, colorimetric assays) suffer from non-specificity and interference. Considering the importance of the biological and pathophysiological roles of sialic acid, development of simple and sensitive methods for the detection of this monosaccharide is poised to make a significant impact in a variety of scientific applications.

Embodiments are directed to methods and compositions for detecting cancer, in particular breast cancer, using silver nanoparticles to induce Surface Enhanced Raman Scattering (SERS) to reveal the presence of sialic acid. Sialic acid is increased in cancers other than breast cancer. It has been established that in many cancer cells the glycoproteins are rich in Sialic acid. Sialic acid increase has also been detected in colon, prostate, uterus, stomach and lung cancer as well. Therefore a number of cancers can be detected by SERS method described herein.

Surface-enhanced Raman scattering is a Raman spectroscopic technique that has potential as a molecularly specific analytic probe for highly sensitive detection of weak Raman signal of analytes at low concentrations or having a low Raman scattering cross-section. It is generally agreed that the dominant contributor to SERS processes is the long-range electromagnetic (EM) enhancement mechanism (7). The enhancement originates from the amplification of light by excitation of either extended surface plasmon resonances on continuous surfaces (8) or localized surface plasmon (LSP) resonances on isolated metal-particle surfaces (9). The second mechanism contributing to signal enhancement is short-range chemical (CM) enhancement, which involves changes in the adsorbate electronic states owing to chemisorption of the analyte (10). In most cases, both EM and CM mechanisms exist simultaneously, in which the former contributes with up to $10^{12}$ enhancement while the latter is thought to be usually of the order $10^2$ (11).

The SERS effect was first observed on uneven metal films with regions of high curvature and gaps between metal grains (so-called "hot spots"), where the confined electromagnetic fields were believed to originate from LSPs exited in these areas (12). If molecules of analyte are placed in the narrow "hot spots" between nanoparticles and illuminated by the excitation light, then the intensity of the Raman scattered light can be enhanced even $10^{15}$ fold. This phenomenon of enhancement was first reported in 1996 by two independent research groups and called single molecules SERS (13, 14).

Because metal nanoparticles exhibit both tunable LSPs and radii of curvature that can generate hot spots, a remarkably wide variety of SERS active metal nanoparticle-based substrates and media have been explored in the last few decades. Colloidal suspensions of nano-sized silver are the most common SERS substrates due to their ease of preparation, long lifetime and high Raman signal enhancement factor which can be excited from the UV to the infrared spectral region. One of the silver colloids used most widely is prepared by the reduction of silver nitrate with trisodium citrate (15, 16). The surface of the citrate-reduced silver nanoparticle (cit-AgNP) is covered by a Stern layer of negative citrate-ions to overcompensate for the positive charge of the nanoparticle surface. This outer Stern layer results in the measured negative zeta ($\zeta$) potential for the whole nanoparticle, generating a repulsive force between the particles and preventing their aggregation. With the knowledge that the surface of the citrate-stabilized AgNPs is negatively charged, it has been demonstrated to be effective in SERS detection of positively charged analytes that can be readily adsorbed onto the colloid surface layer (17, 18). Negatively charged compounds generally do not give intense SERS signals with cit-AgNPs, and furthermore, citrate bands are also absent. Consequently, most of the published SERS studies of anionic analytes have used citrate-reduced silver colloids treated with surface-modifying agents (such as poly-L-lysine combined ascorbic acid (19)), colloids that were prepared using different reduction agents (20), or electrochemically roughened Ag/Au electrodes (21). However, some previous studies have shown that anions will bind to the surface of cit-AgNPs without any modifying cationic coating (19, 22). The use of SERS in analytical procedures requires control of properties as adhesion and molecular orientation on the surface. Thus, further understanding of factors and conditions that determine interaction of negatively charged silver nanoparticles with potential analytes is of importance for qualitative and quantitative analysis by SERS.

II. Kits

In some embodiments, the present invention provides kits and systems for use in monitoring the level of sialic acid in an individual. In certain aspects kits are for use by medical professionals. For example, in some embodiments, the present invention provides kits for monitoring subjects suspected of having or diagnosed as having cancer. In yet other embodiments, the present invention provides systems comprising cit-Ag nanoparticles and optionally sialic acid controls. In certain aspects the cit-Ag nanoparticles are used as described herein and a device is used to take readings and measure the sialic acid levels in a sample. In some embodiments, an entire system is provided that comprises a sensor, a detection device, and cit-Ag nanoparticles. Other kits may supply the one or more of: (i) reagents to form the cit-AG nanoparticles, (ii) the cit-Ag nanoparticles, (iii) sample processing reagents, (iv) sampling device (e.g., cotton swab), and, (v) controls or standards for comparison or calibration.

III. Examples

The following examples as well as the figures are included to demonstrate embodiments of the invention. It should be appreciated by those of skill in the art that the techniques disclosed in the examples or figures represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

Calculations, equipment, methods of calculations, chemicals selected and other items used for testing purposes of this invention are not limited to those selected but may include comparable materials and methods.

Example 1

Surface-Enhanced Raman Scattering of N-Acetylneuraminic (Neu 5Ac) Acid on Silver Nanoparticle Surface Silver nanoparticles synthesis and characterization. All reagents were purchased from Sigma-Aldrich, of analytical grade, and were used without further purification. Silver NPs capped with citrate were obtained using the Turkevich method (24). A solution of silver nitrate (2.5 mM) in deionized water was heated to 95 degrees Celsius, and a solution of trisodium citrate (2.5 mM) was added. Nearly 15 min later, the color of the solution turned into grayish yellow, indicating the formation of nanoparticles. After cooling the solution to room temperature, the obtained silver nanoparticles AgNPs were washed by centrifugation-redispersion cycles with deionized water three times and stored in the dark until used.

HR-TEM images of AgNPs were obtained with JEOL 2010-F transmission electron microscope operating at 200 kV. Samples were prepared by dropping a colloidal dispersion of AgNPs onto a carbon-coated copper grid and dried in air. Optical absorbance spectra were recorded with a Cary 100 Uv-Vis spectrophotometer (Agilent Technologies) in the range 200-800 nm. The silver concentration was determined using the method of atomic absorption spectroscopy (AAS, Shimadzu AA-6200).

Raman and SERS measurements.

Raman spectra were measured with an iHR 320 Horiba Jobin Yvon spectrometer using laser excitation with a wavelength at 785 nm and output power of 25 mW. This instrument was equipped with an Olympus BX41 optical microscope, and a thermoelectrically cooled charge coupled detector (Synapse CCD Detection System) with 1024×256 pixel format, operating at −70 degrees Celsius. The signal was calibrated by using the 520 cm-1 line of a silicon wafer and a 10× objective. The spot size was about 3.8 μm.

The Neu5Ac solutions with different concentrations were prepared by serial dilutions of a $2\times10^{-2}$ M stock solution in water. For all of the SERS measurements, 10 μl of an aqueous solution of Neu5Ac were added to an equal volume of the silver colloid ($1.4\times10^{-4}$ M), the resulting mixture was then deposited onto a quartz slide and dried at room temperature. Five to eight SERS spectra were collected with an exposure time of 2 s at different illumination spots for each substrate investigated.

In certain aspects the methods described herein can be used to analyze sample sizes in the range of 1 to 10 μL or larger. In certain aspects, sample sizes smaller than 1 μL are possible, however the limiting factor for further reduction of the sample size is the technical difficulty in handling of a very small sample.

The most commonly used substrates in Raman applications are silicon, glass, and quartz. Some embodiments use a quartz microscope slide as a substrate with a low background and fluorescent spectral features in the wavenumber region of interest. Because pure metals are known to have no Raman spectral features and very low background signal, a metallic substrate (e.g. aluminum sheet) can be a suitable substrate that can replace the quartz slide.

Some embodiments of the disclosed invention have recorded SERS spectra from solutions containing $10^{-7}$ M Neu5Ac concentrations without any particular effort to improve the signal (low laser power and short exposure time). Using a higher laser power or longer exposure time and number of accumulations may increase the SERS intensity and improve the signal-to-noise ratio of the spectra, although the detection time may increase. Furthermore, for the creation of a calibrating curve relating SERS intensity to concentration, a consistent laser power should be considered. Some embodiments of the disclosed invention use a natural air-drying process (20 min at 25° C.) that provides a sufficient time period to ensure that adsorption has taken place.

Theoretical Calculations.

The DFT calculations were carried out in gas phase using Gaussian 03 program (25). The methodology includes the generalized gradient approximation (GGA) with Perdew-Burke-Ernzerhof (PBE) exchange-correlation functional (26) and a 6-31G(d,p) basis set for C, N, O, H atoms (27). Mentioned basis set includes diffuse functions for a better prediction of the Raman intensities (28). Structural optimization of isolated and adsorbed neu5Ac molecule was performed with no symmetry restrictions, using a force tolerance criterion of 0.01 eV/Å. After considering various orientations of the Neu5Ac molecule adsorbed on the silver cluster, the lowest-energy structure is discussed. In order to correlate calculated frequencies with experimental data a 0.96 scale factor has been applied, leading to an agreement both in position an intensity of Raman active modes.

The transmission electron microscopy (TEM) images of the citrate-capped AgNPs are represented in FIG. 1A. The TEM data indicate that most of the particles are isolated and well-faceted, ranging in size from 2 to 10 nm (FIG. 1A). The TEM micrographs illustrated in FIG. 1A show a single AgNP surrounded by a layer of organic matrix, providing evidence for uniform ligand surface coverage of thickness from 2 to 5 nm. The UV-Vis spectrum of the citrate-capped silver nanoparticles (FIG. 1B) showed an absorption band with a maximum located at 403 nm, arising from the surface plasmon resonance of the AgNPs.

Figure 2:
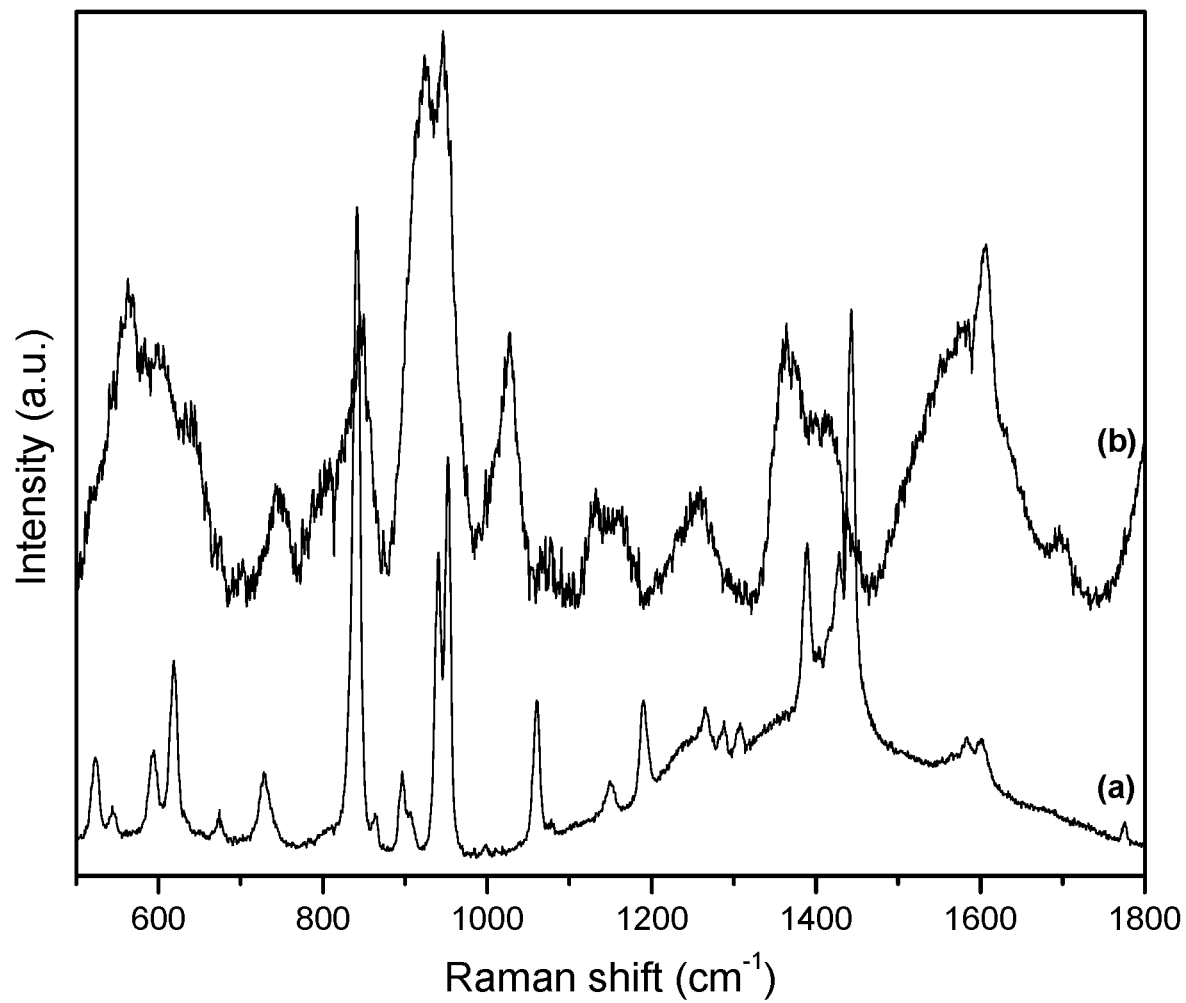
FIG. 2. Raman spectrum of solid sodium citrate (A) and SERS spectrum of citrate-AgNPs colloidal solution (B).

The Raman and SERS spectra of sodium citrate are displayed in FIG. 2. The assignment of the main band is made based on previously reported Raman spectra of sodium citrate and related compounds (19, 29, 30). The vibrational modes are considerably broader and blue shifted in the SERS spectrum, suggesting a substantial interaction of citrate ion with metal surface. Considering that citrate ion is relatively "hard" ligand, its interaction with AgNPs is most likely to be electrostatic in nature and can be described in terms of EM SERS mechanism. The most strongly enhanced bands of cit-AgNPs are located at 563, 924, 952, 1023 and 1607 cm$^{-1}$ (Table 1). These modes are ascribed to the anchoring carboxylate groups located in the field of the silver surface plasmon, as expected for the EM SERS mechanism. These results are in accordance with a binding geometry proposed by Munro et al. in which two carboxyl groups of citrate are attached to silver colloid surface (19).

TABLE 1

Wavenumbers and band assignments of the main Raman and SERS bands of sodium citrate.

| Raman mode (cm$^{-1}$) | SERS mode (cm$^{-1}$) | Description | Raman mode (cm$^{-1}$) | SERS mode (cm$^{-1}$) | Description |
|---|---|---|---|---|---|
| 523 | — | $\gamma(CO_2)$ | 940 | 924 | $\nu(C-CO_2) + \rho(CH_2)$ |
| 544 | — | $\delta(C-C-C)$ | 952 | 946 | $\nu(C-C-O)$ |
| 594 | 563 | $\delta(CO_2)$ | 1060 | 1027 | $\nu(C-O)$ |
| 619 | 600 | $\omega(CO_2)$ | 1190 | 1147 | $\nu(C-C-O)$ |
| 674 | — | $\delta(CO_2)$ | 1288 | 1259 | $\nu(C-O) + \delta(O-H)$ |
| 729 | 743 | $\rho(CH_2)$ | 1389 | 1364 | $\nu(CO_2)$, sym + $\delta(CH_2) + \omega(CH_2)$ |
| 841 | 845 | $\nu(C_4O)$, sym + $\rho(CH_2)$ | 1428 | — | $\nu(C-O) + \delta(O-H) + \nu(CO_2)$, sym |
| 896 | — | $\nu(C-CO_2) + \nu(C-C)$ | 1443 | — | $\delta(CH_2)$, asym |
|  |  |  | 1601 | 1607 | $\nu(CO_2)$, asym |

Abbreviations:
$\delta$ = in plane deformation,
$\omega$ = out of plane deformation,
$\gamma$ = wagging,
$\nu$ = stretching,
$\rho$ = rocking,
$\tau$ = twisting,
sym = symmetric,
asym = asymmetric.

Relaxed structure of Neu5Ac is formed by carboxyl, hydroxyl, N-acetyl, and a linear chain that resembles glycerol structure. There are 40 bonds contained in the length range of 0.98 to 1.57 Å and distributed as follows: six O—H bonds (around 0.98 Å); one N—H bond of 1.02 Å; 13 C—H bonds (1.1 Å); one C=O bond of carboxyl (1.22 Å) which is 1.24 Å in the amide group; one C—O bond of carboxyl of 1.35 Å; two N—C bonds which are 1.36 and 1.47 Å being shorter the bond between N and carboxyl group; seven C—O bonds of hydroxyls around 1.42 Å, and 9 C—C bonds in the range 1.52-1.57 Å. The molecule of Neu5Ac belongs to the C1 point group, and its 114 normal vibrational modes are infrared and Raman active.

Figure 3:
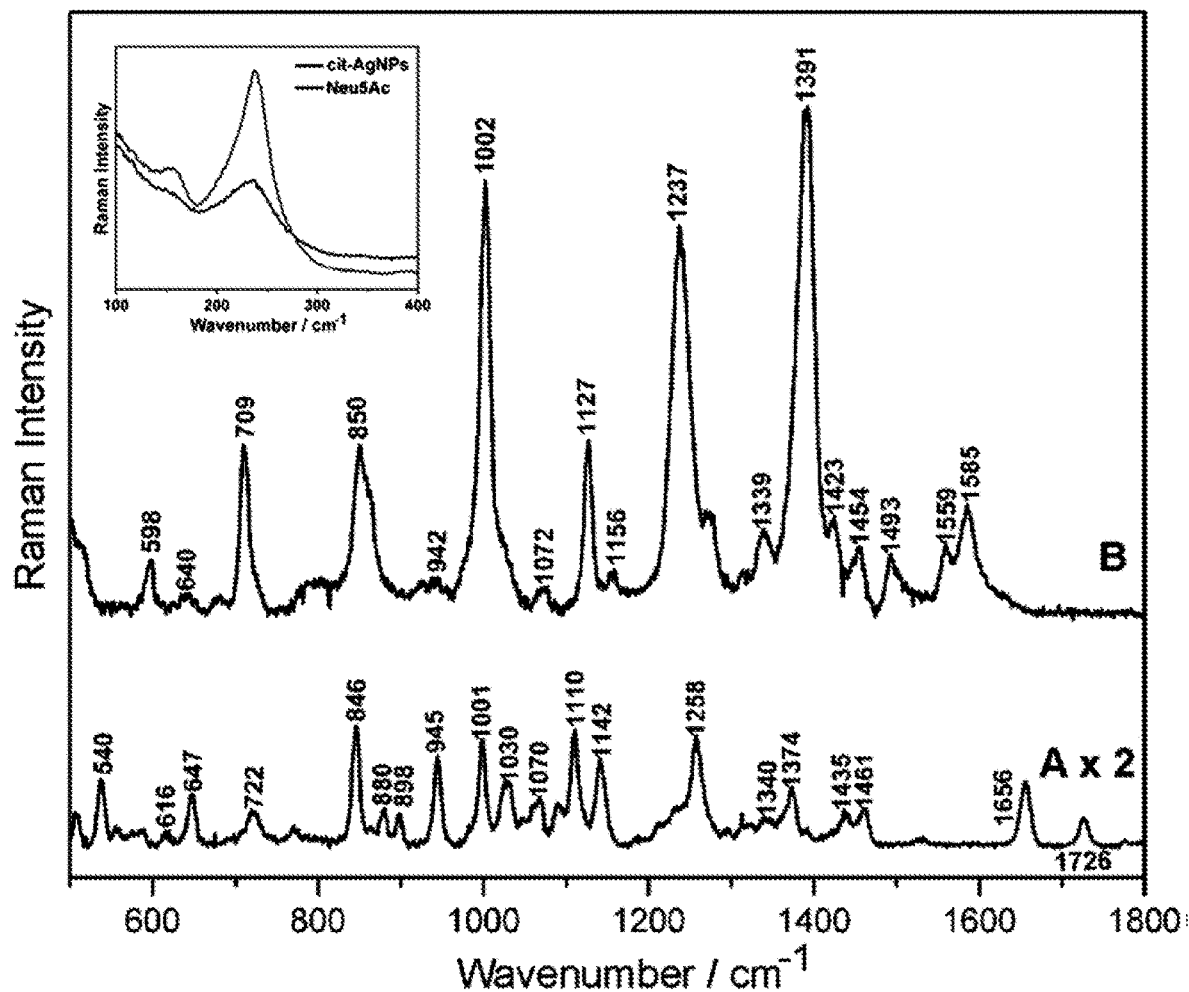
FIG. 3. Raman spectrum of solid Neu5Ac (A) and SERS spectrum of $10^{-4}$ M Neu5Ac on cit-AgNPs (B). The band of the inset belongs to the vibrations of Ag—O and Ag—N bonds.
Figure 4:
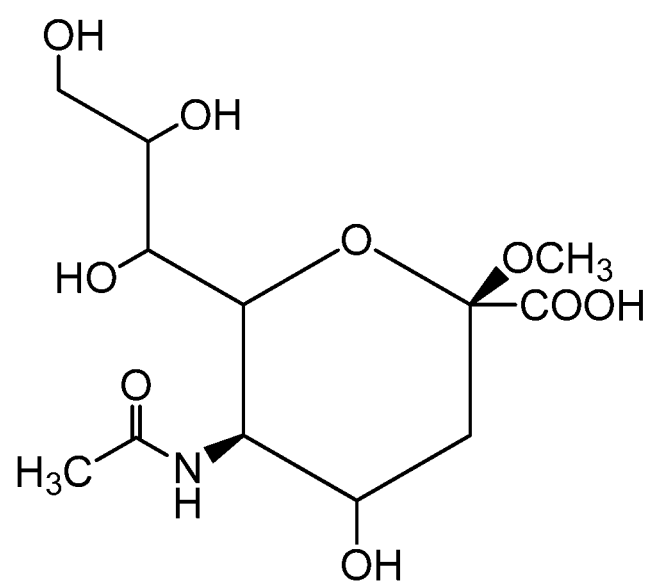
FIG. 4. Chemical structure of Neu5Ac.
Figure 5:
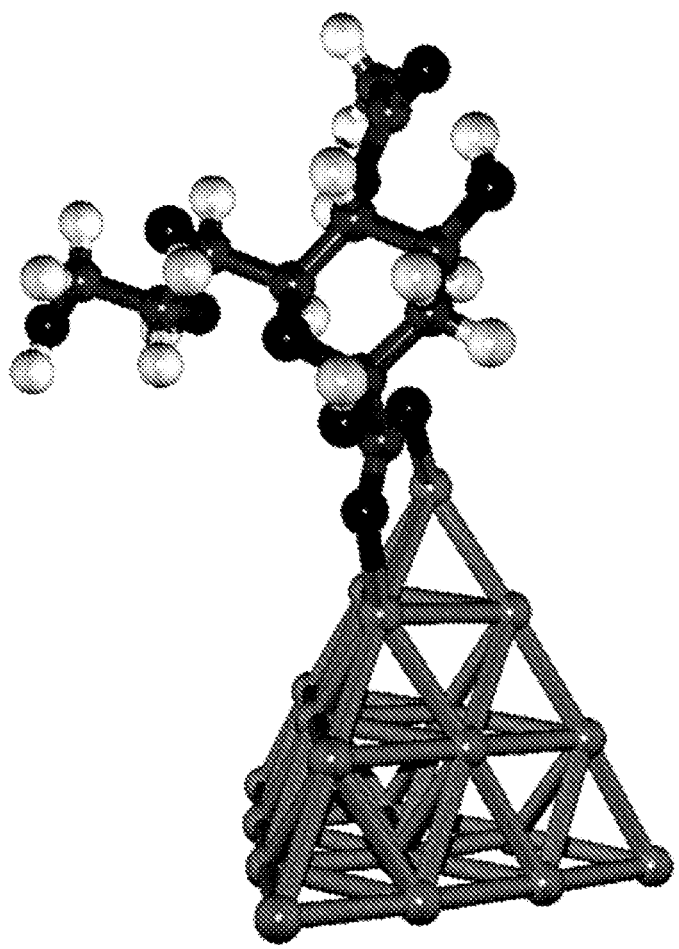
FIG. 5. Optimized geometry of the lowest energy molecule arrangement of the Neu5Ac on the Ag20 cluster surface.

The experimental Raman and SERS spectra of Neu5Ac are shown in FIG. 3. The vibrational frequencies observed in the spectra along with their proposed assignments are listed in the Table 2. Assignment of the fundamental bands is based on the comparison with related molecules and on DFT calculations. The spectrum of Neu5Ac in its neat solid state (FIG. 3) reveals a number of features characteristic for Raman spectra of carbohydrates (47). The fingerprint wavenumber region of the spectrum (500-1800 $cm^{-1}$) can be divided into three main spectral ranges: (1) The 500-950 $cm^{-1}$, vibrations due to CO(CH) groups or their substitutes in pyranose ring; (2) 950-1200 $cm^{-1}$, C—O stretching mode with some contribution of the skeletal C—C stretching vibrations and (3) 1200-1500 $cm^{-1}$, deformational vibrations such as involving HCH and $CH_2OH$ functionalities. No bands in the amide-II characteristic spectral range (1500-1600 $cm^{-1}$) were observed. Oleinikov et al. (48, 49) reported the Raman spectra of the glycosides of Neu5Ac, such as α-methylglycoside (FIG. 6), and proposed that the strong band at 873 $cm^{-1}$ assigned to the glycerol fragment vibrations can be used as a Raman marker of sialic acid. Under the experimental conditions of this invention the abovementioned band is of medium intensity and the Raman spectrum of solid Neu5Ac is rather dominated by the bands around 846, 1001, 1110 and 1258 $cm^{-1}$, which have been assigned to the C—H vibration, ring breathing, C—O—C deformation and amide III mode, respectively.

TABLE 2

Vibrational mode assignments for Raman and SERS spectra of Neu5Ac.

| Raman experimental mode ($cm^{-1}$) | Raman calculated mode ($cm^{-1}$) | SERS experimental mode ($cm^{-1}$) | Description | Reference number |
|---|---|---|---|---|
| 540s | 581.2 | — | δ(C—O—C) in ring + ρ(O—H) in glycerol* | 31 |
| 616w | 639.9 | 598m | δ($CO_2$) + δ(OH)* | 32 |
| 649s | 680 | 640w | δ(ring) + ρ($CH_2$), ring* | 33 |
| 722m | 742.6 | 709s | δ($CO_2$) + γ(C)* + γ(H) of hydroxyl* | 34 |
| 770w | 808.4 | — | δ(C—C—O), δ(C—C—H), δ(O—C—H) + γ(H) of carboxyl and hydroxyl* | 32 |
| 846vs | 874.3 | 850s | δ(C—H), equatorial + ρ($CH_2$) in glycerol chain* | 33 |
| 880m | 929.7 | — | ν(C—O—C) + ν(C—C)* | 34 |
| 898m | 947.2 | — | δ(C—H) axial + τ(C—$H_2$) in ring* | 35 |
| 945s | 986 | 942w | ν(C—O—C) + ν(C—O) in glycerol chain* | |
| 1001vs | 1037.81 | 1002vs | ν(C—C) in ring, ν(C—N)* | |
| 1030s | 1045.7 | — | ν(O—C), ν(C—C) in glycerol chain* | |
| 1070m | 1077.2 | 1072w | δ(C—H), δ(C—O—H) + ν(C—O—C) in ring, asym* | 37 |
| 1094m | 1094 | — | ν(C—C) in ring, sym + ν(C—O)* | 38, 39 |
| 1110vs | 1161.7 | 1127s | ν(C—C), ν(C—O) asym | 39 |
| 1142s | 1147.3 | 1156w | τ($CH_2$)* | |
| 1234sh | 1250.6 | 1237vs | ⎤ | |
| 1258vs | 1250.6 | — | ⎬ ν(C—N), Amide III | 38, 40, 41 |
| 1296vw | 1294.3 | — | ⎦ | |
| 1340w | 1372.2 | 1339m | γ($CH_2$)* + δ(C—O—H) | 42 |
| 1374m | 1391.8 | — | ν(C—C)* | |
| 1390vw | 1440 | 1391vs | ν($CO_2$) | 43 |
| 1435m | 1450.5 | 1423m | δ(C—H)* | |
| 1460m | 1453.3 | 1454m | δ($CH_2$) | 44 |
| 1532vw | 1511 | — | ν(C—N)* | |
| 1656s | 1696.2 | — | ν(C=O), Amide I | 45 |
| 1726m | 1804.2 | — | ν(C=O) | 46 |

Abbreviations:
δ = deformation,
γ = wagging,
ν = stretching,
ρ = rocking,
τ = twisting;
sym = symmetric,
asym = asymmetric.
Intensities of Raman lines:
vw—very week,
w—week,
m—medium,
s—strong,
vs—very strong,
sh—shoulder.
*assignment based on the DFT calculations.

Figure 6:
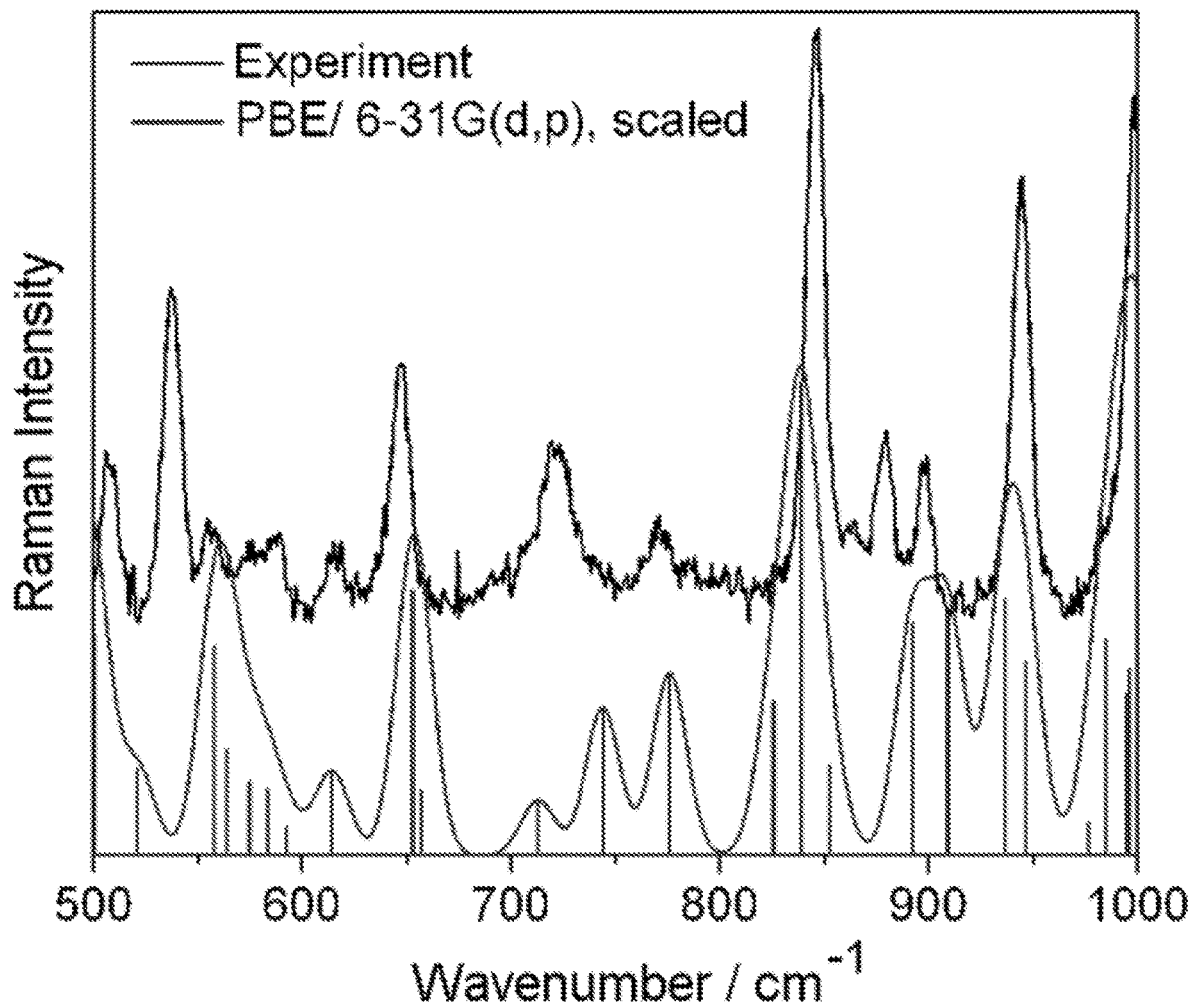
FIG. 6. Comparison between experimental and PBE/6-31G(d,p) calculated Raman spectra in the wavelength range from 500 to 1000 $cm^{-1}$.

The calculated Raman spectral pattern of Neu5Ac in gas phase is in agreement with the experimental data. Comparison between scaled Raman spectrum in gas phase and the measured one is depicted in FIG. 6. The calculated Raman spectrum of Neu5Ac shows intense peaks at 537, 649, 846, 880, 945 and 1001 cm$^{-1}$. In addition to the vibration modes described before, the bands at 537 and 945 cm$^{-1}$ are related to the O—H bending and C—O stretching modes in the glycerol chain, while the peak located at 649 cm$^{-1}$ is assigned to the CH$_2$ rocking mode in the pyranose cycle (Table 2).

Figure 7:
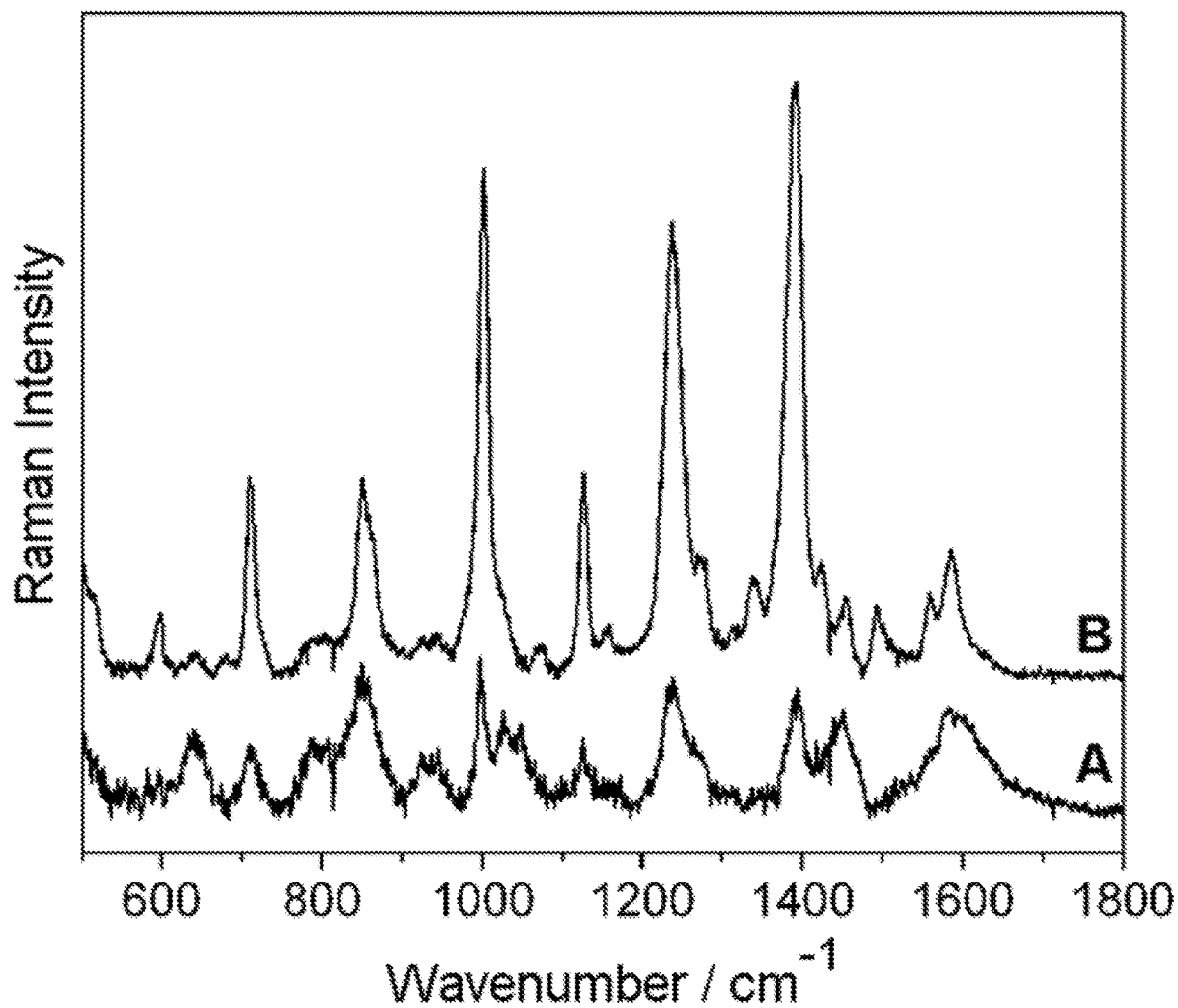
FIG. 7. Comparison of the SERS spectra obtained at $10^{-7}$ M (A) and $10^{-4}$ M (B) concentrations of Neu5Ac.

The SERS spectrum of Neu5Ac ($10^{-4}$ M) adsorbed on silver nanoparticle surface is shown in FIG. 7. An enhancement factor was achieved using the drop coating deposition Raman (DCDR) method (50, 51). A small aliquot containing silver colloid mixed with Neu5Ac was deposited on a quartz slide to produce the concentrated evaporation residue. Formation of such ring-like structure along the edge part of the drop is caused by the "coffee ring effect" (52) and was observed for various concentrations of Neu5Ac, allowing detection down to the limit of $10^{-7}$ M (FIG. 7). This drying process promotes binding of some analytes onto the SERS-active surface as well as concentrates them in the ring, (53, 54) providing the possibility to obtain clearly identifiable Raman spectra with a laser power of 25 mW in only 2 s.

Significant differences are observed in the SERS spectrum of Neu5Ac respect to the normal Raman spectrum in the solid state with selective enhancement of some of the Raman bands. These differences are caused by substantial variations in molecular electronic shell due to adsorption of the analyte followed by change in force constants and polarizabilities. The SERS spectrum of Neu5Ac most notably contains bands at 1002, 1237 and 1391 cm$^{-1}$, attributed to the vibrations of pyranose ring, acetamide, and C—H groups. The low frequency region of the spectrum is represented by the peaks around 598, 709 and 850 cm$^{-1}$ arising from carboxyl group and equatorial C—H deformation. These findings are consistent with earlier studies which have demonstrated the importance of pyranose ring, carboxyl, and acetamide groups during the adsorption of sialosides onto a SERS active surface (55, 56). The bands at 1559 and 1585 cm$^{-1}$ have been assigned to residual citrate ions.

FIG. 7 shows a representative SERS spectrum collected from the drop with Neu5Ac concentration of $10^{-7}$ M. Although an irregular distribution of SERS intensity over the edge area of the drop is observed, it is important to notice that several SERS spectra were recorded over the area. As expected, on diminishing the analyte concentration the overall intensity of the SERS bands decreases.

To further investigate the adsorption mechanism, the intensity of the band around 237 cm$^{-1}$ observed in the SERS spectrum of cit-AgNPs was compared to that in the SERS spectrum of Neu5Ac. This peak is attributed to the stretching vibrations of Ag—O (57) and Ag—N(58, 59) bonds. As one can see, the SERS intensity of this peak for Neu5Ac is roughly three times as strong as that for cit-AgNPs, suggesting the adsorption of Neu5Ac on the AgNPs surface either through carboxyl or amide group, or both. Thereafter, a tetrahedral twenty-atom fragment of the face-centered (fcc) silver crystal lattice (Ag20) was adopted and used the DFT method to study the interaction of neu5Ac with this cluster. The optimized adsorption geometry suggests that the binding of Neu5Ac to the Ag20 surface most likely occurs through both oxygen atoms of the carboxyl group whereas the COOH plane aligned along one of the edges of the Ag cluster.

Recently, Wagener et al. have shown that a citrate concentration higher than 50 μM applied during the synthesis of cit-AgNPs results in an almost covered nanoparticle surface with no ligand-free faces available (60). These findings are fully supported by our TEM results that revealed the presence of a continuous layer of adsorbed citrate anions surrounding the nanoparticles. Therefore, in order to generate the SERS effect, the Neu5Ac molecules have to cross an energetic barrier caused by electrostatic repulsion of citrate shell before they can be either directly adsorbed on the positively charged nanoparticles or stay in the very near vicinity (less than 10 Å (61)) of their surface. Consequently, in the adsorption process of Neu5Ac to cit-AgNPs, there will be competition between two negatively charged ions for surface sites. The factor that determines which of the ions binds more effectively to the surface, and thus gives the larger signal intensity, is the free energy change associated with replacing one anion bound to the silver surface by a different anion. The binding energy of citrate and Neu5Ac on the Ag20 cluster has been compared via calculation of Total Energies difference before and after the adsorption of molecules on the Ag20 cluster. The relative binding energies (BE) of citrate and Neu5Ac to the silver cluster are taken as measures of the relative strength of their interactions. In the case of citrate, the inventors have considered the interaction through carboxyl group that has been recently reported as the most probable mechanism (62, 63). The BE of citrate and Neu5Ac were found to be 1.34 and 1.81 eV, respectively. The higher BE provides Neu5Ac with an advantage over citrate in competitive binding to silver, supporting the SERS results that demonstrated the appearance of the vibrational modes belonging to the added Neu5Ac.

Disclosed herein is a method for a label-free detection of Neu5Ac using unmodified citrate-reduced silver nanoparticles. A DFT-calculated higher affinity of Neu5Ac for the silver nanoparticle surface results in replacement of the adsorbed citrate and supports the results obtained by SERS spectroscopy. The inventors have recorded SERS spectra from solutions containing $10^{-7}$ M Neu5Ac concentrations without any particular effort to improve the signal. Therefore, the inventors provide a versatile route to develop a highly sensitive SERS-based technique for detection of Neu5Ac, which is sought for a range of biomedical applications.

Example 2

Detection in Clinical Samples

A. Results

SERS Results of SA-AgNPs.

Initial calibrations were performed to establish optimal, easily reproducible conditions to measure the SA-SERS in the presence of the AgNPs, and the viability to determine from the SERS the SA concentration interpolating from the experimental data. With that aim preliminary solutions of SA in distilled water were prepared in final concentrations of 1, 5, 10, 20, 50, 100, 150 and 200 mg/dl, and the SERS of each of these concentrations were recorded.

Figure 8:
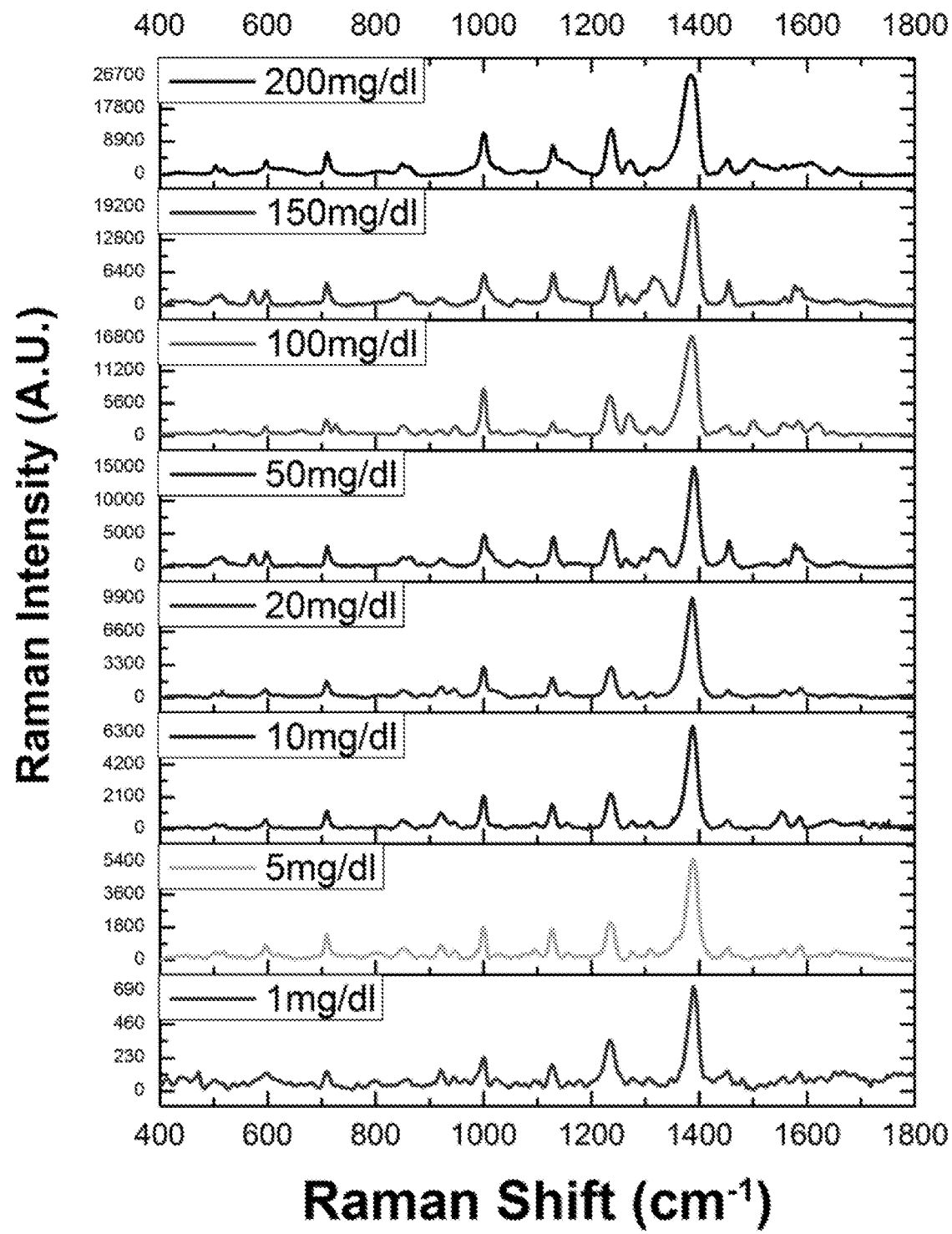
FIG. 8. Raman spectra of various concentrations Neu5Ac.

SERS of the SA in the presence of the citrate AgNPs was determined at five different concentrations from 20 to 200 mg/dl (FIG. 8). SERS were also recorded for SA concentrations from 1, 5, 10, and 15 mg/dl (not shown), that exhibit very similar features when scaled to their respective differences in intensity. The spectral features in all these SERS are almost identical to those reported and identified by Vinogradova et al. (67). The three stronger peaks in intensity where selected at spectral positions of 1002, 1237 and 1391 cm$^{-1}$, which correspond to the breathing mode of the pyranose ring, to the v(C—N) stretching mode of Amide, and to the v(CO$_2$) stretching mode of the carboxyl radical, respectively; all these constitutive components of the SA molecule.

Figure 10A:
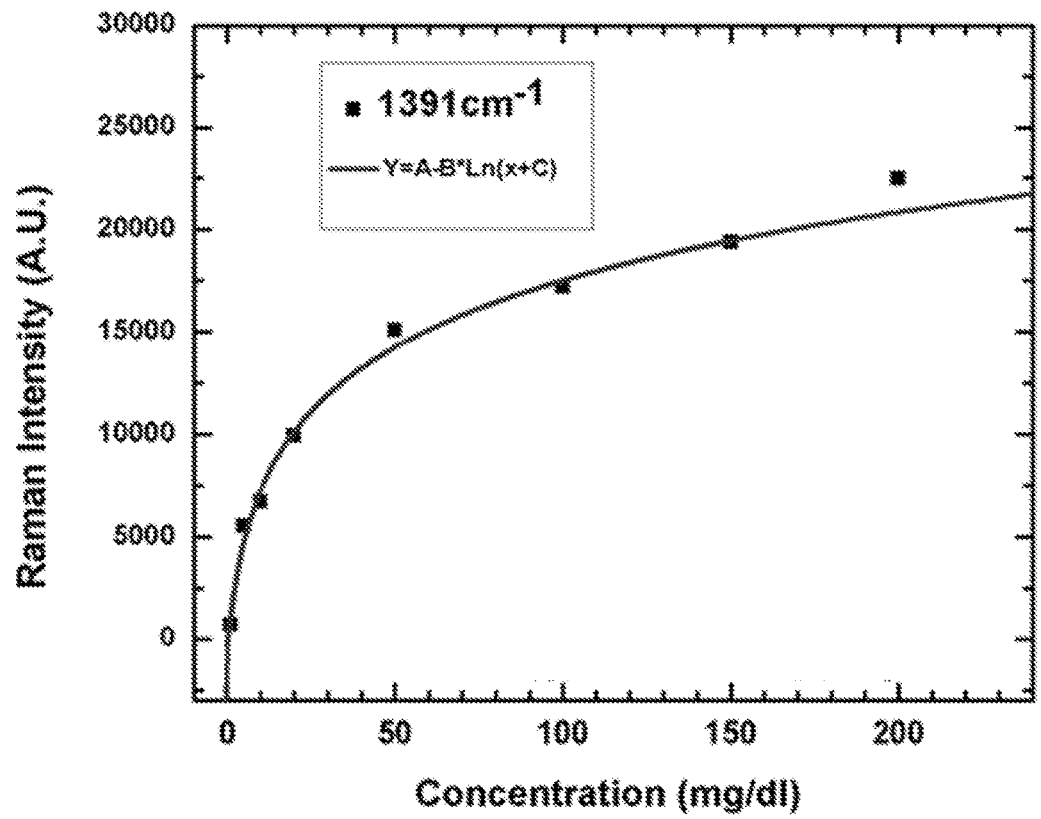
FIGS. 10A-B. Plot of the intensity of the three main SERS lines of the citrate-AgNPs in the presence of Neu5Ac in increasing concentrations, 1 to 200 mg/dl, dissolved in deionized water.
Figure 10B:
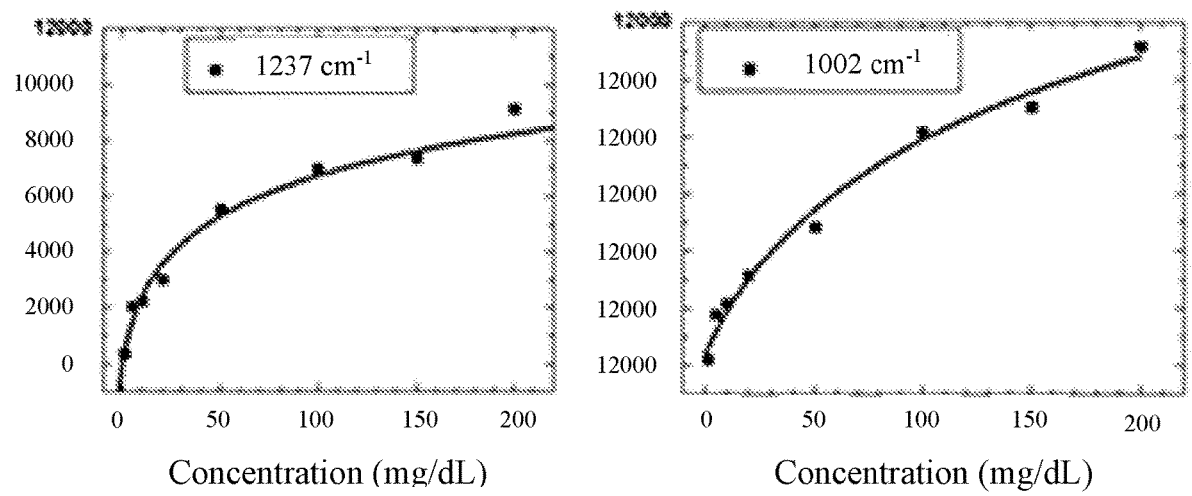

There exists a monotonic increase of the SERS intensity correlated with the SA concentration adsorbed on the AgNPs in the colloidal suspension. A plot of the count intensities of the three A, B and C lines is shown in FIGS. 10A-B. The resultant fits result in a high degree of correlation, larger than 0.98 for these three dominant lines, which are shown mainly to highlight the increasing signal trend correlated with the amount of dissolved SA, and hence, the possibility that given a SERS signal of SA any intermediate concentration between the plotted intensities may be interpolated and determined.

Figure 11:
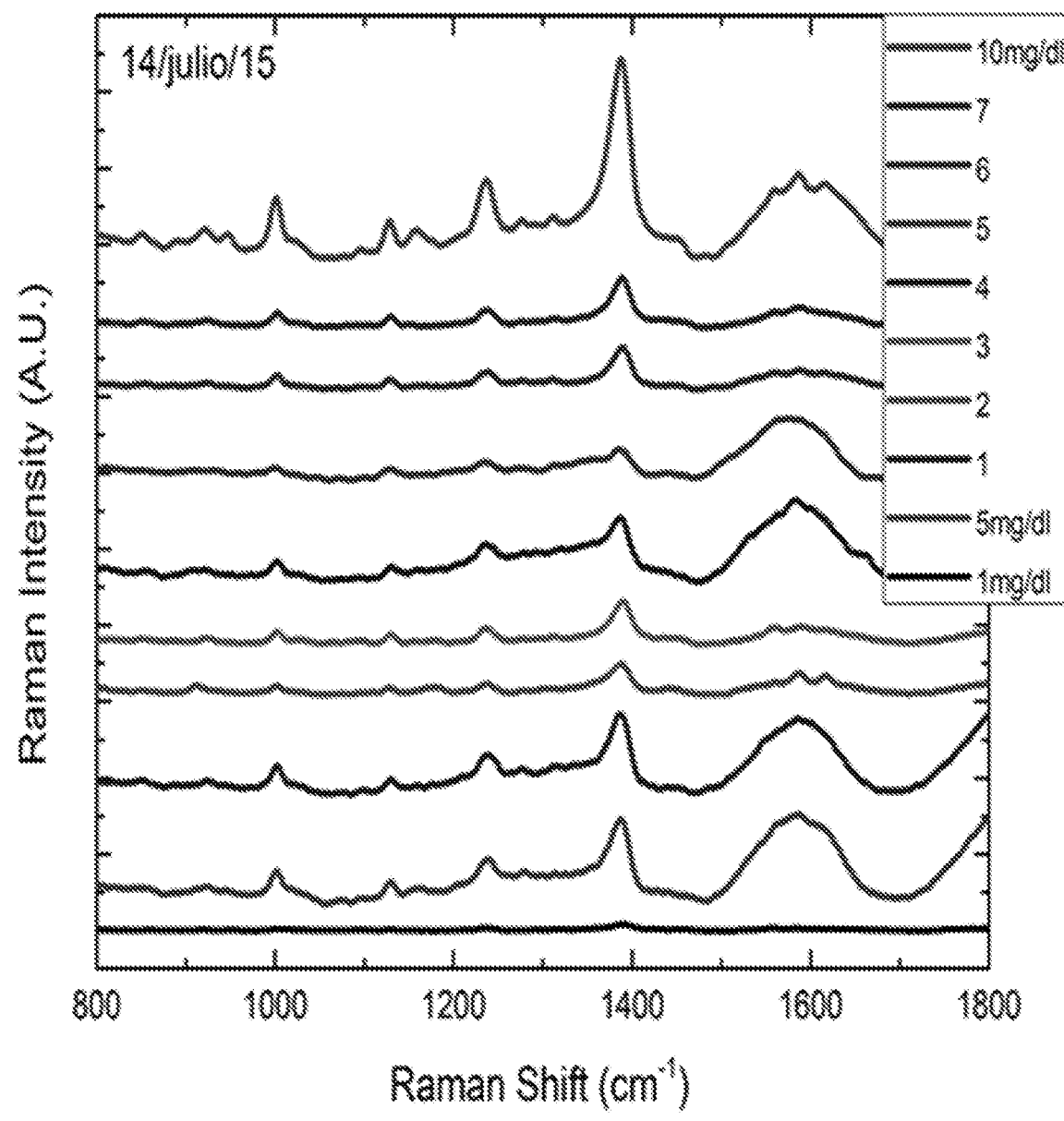
FIG. 11. Comparison between the SERS of sialic acid at concentrations 1, 5 and 10 mg/dl and that of the SA from saliva in seven healthy women.

In FIG. 11 a comparison between the SERS of pure SA at concentrations 1, 5, and 10 mg/dl, measured for calibration in the same programmed run and that of SA from saliva in seven adult females is shown. A perusing of these spectra immediately shows that the SERS of the saliva is very similar to that of pure SA. Hence it validates the capacity to calibrate the actual SA concentrations by the relative intensity of the three most intense Raman lines. From the SERS intensities of the seven healthy patients it is perceptible how their SA concentration has to lie somewhere in values intermediate between 1 and 5 mg/dl.

Figure 12:
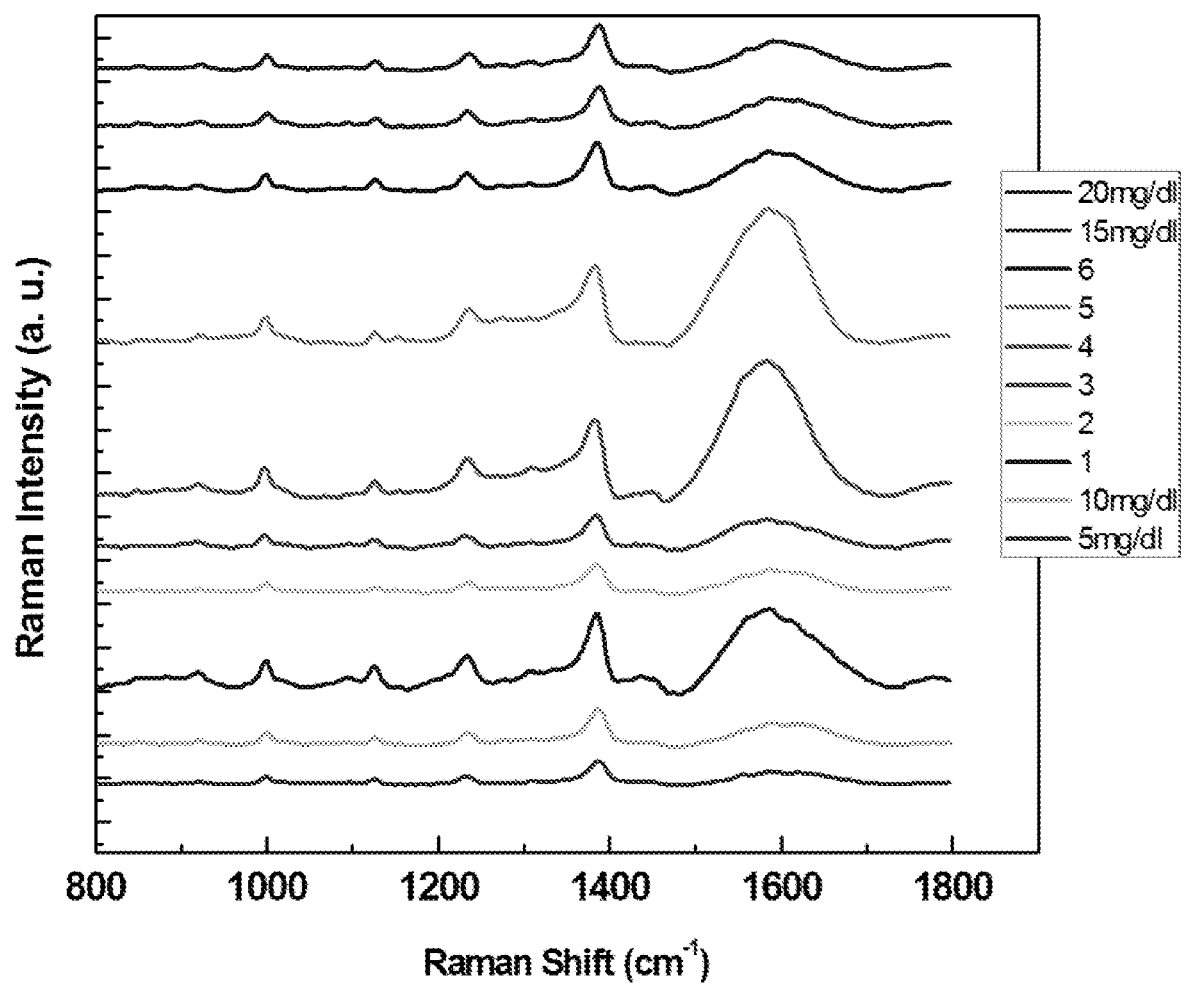
FIG. 12. Comparison between the SERS of sialic acid at concentrations 5, 10, 15 and 20 mg/dl and that of the SA from saliva in six breast cancer patients.

In FIG. 12 a similar comparison between the SERS of pure SA at concentrations 5, 10, 15 and 20 mg/dl and that of the SA from saliva in six breast cancer patients is shown. Now in contrast to the case for the SERS from healthy individuals, it may be appreciated that the SA concentrations in the saliva of these sick patients have values between 10 and 20 mg/dl, instead of values smaller than 5 mg/dl, for the healthy women.

Calibration of Sialic Acid Concentrations.

Figure 9:
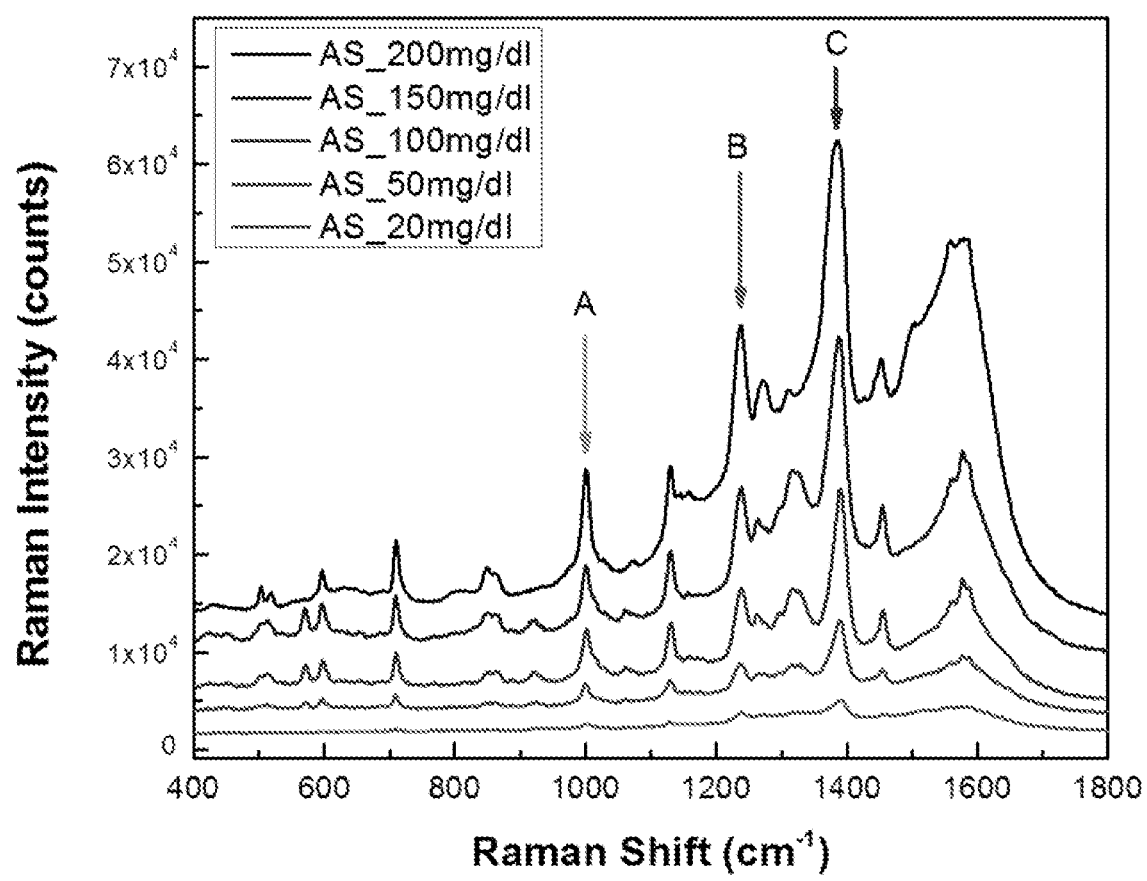
FIG. 9. SERS of citrate-AgNPs in the presence of Neu5Ac in increasing concentrations, 20 to 200 mg/dl, dissolved in deionized water.

The SA concentration interpolated values may be calculated from either a logarithmic fit y=a−b ln [x+c], where a, b and c, are fitting parameters or from two straight lines, the first, from 1 to 20 mg/dl, and the second from 20 to 50 or 200 mg/dl. Both procedures provide good fits and resultant concentrations that coincide on average within ±0.5 mg/dl. As the intensity of the three lines increases at different rates with the SA concentration, the actual calibration is calculated from the average values estimated from the three A, B and C lines of FIG. 9. The final uncertainty in the average results in a conservative determination of the SA concentration within ±1.0 mg/dl.

Determination of SA Concentration in Control and Breast Cancer Patients.

Figure 13:
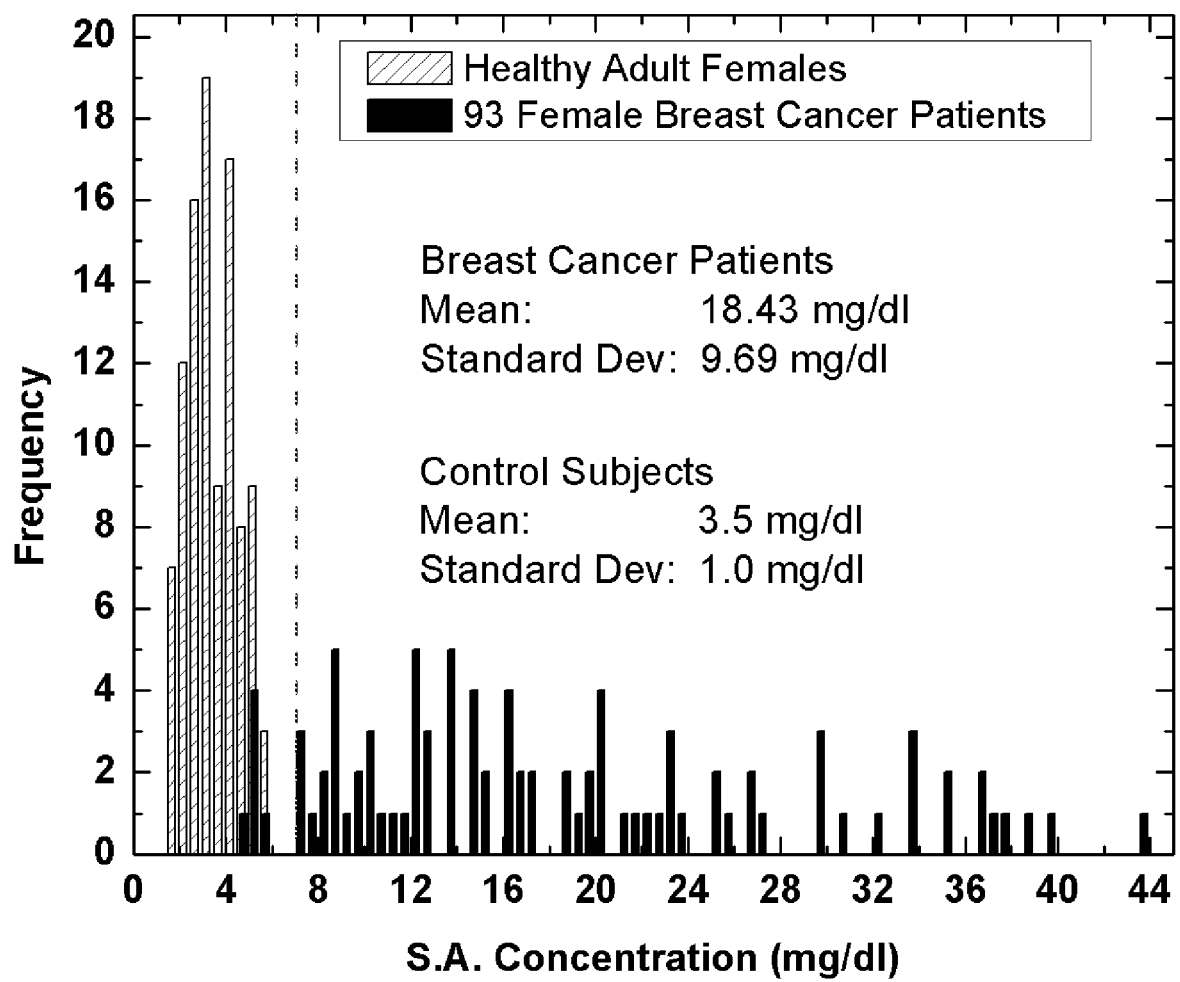
FIG. 13. Illustration of results from clinical studies measuring sialic acid in saliva of control and cancer subjects.

In FIG. 13 a plot of the resultant frequencies for SA concentrations in intervals of 0.5 mg/dl is shown for both control individuals and for all breast cancer patients irrespective of the diagnosed cancer stage. In this Figure, it is immediately apparent how the SA concentrations of the control group of healthy females are tightly clustered following a recognizable normal distribution, of mean 3.5 and S.D. 1 mg/dl. In contrast, for the diagnosed breast cancer patients there exists a broad spread in SA concentrations from 5 to 40 mg/dl, with a mean of 17 and S.D. of 7.5 mg/dl. For the purpose to establish a biological marker indicative of the presence of an ongoing cancer process in an individual, a threshold may be immediately suggested as a medical standard to be adopted from this Figure: any SA concentration determined by a SERS-AgNPs test as described in this report, above 7 mg/dl, may indicate with high probability the presence of breast cancer, requiring further medical examination and possible treatment, when corroborated by any additional alternative analysis applicable.

Breast Cancer Stages.

The large spread in SA for the affected patients suggests that it is necessary to examine if there exists a different expression of the SA correlated with the stage of the breast cancer disease.

Statistical Analysis.

Using the definition of sensitivity as the percentage of positives that are correctly identified, in this study the cancer patients with SA≥7 mg/dl, as discussed before, one calculates for the sensitivity of the proposed SERS-AgNPs tests 0.918, i.e. of the diagnosed patients, the tests gives a true positive result in 91.8% of the cases. From the statistical analysis for the control group, taking the mean of 3.5 mg/dl and the calculated standard deviation of 1 mg/dl, one expects that ≈0.2% (at 3 S.D. above the mean) of healthy individuals exceed the 7 mg/dl threshold. This number defines the percentage of false positives expected.

In statistics, the specificity is defined as the probability that a healthy individual will get a negative result in the test under consideration. Using the same limit of 7 mg/dl, that as discussed is reached only after three standard deviations above the mean, then the specificity results in 99.8%.

There are several definitions for the precision of a test. Among them, the inventors use the definition that precision is the proportion of true positives divided by the number of all positives; considering again the threshold proposed of the 7 mg/dl, results in a very high percentage, 99.8% of precision.

Test Limits.

The possible affectation of the test using saliva for SA determination, by the oral conditions is discussed for instance by Öztürk et. al. (6). They caution in particular that gingivitis may raise the SA concentrations as suggested by previous reports on rats (74), but they do not provide data in humans.

Stefenelli et al. (75), have reported how SA concentrations increase as well in the serum of a large number of subjects examined, in other kinds of cancer, in particular these authors studied the over expression of SA in breast, uterus, lung, colon/rectum, stomach and prostate cancer in the serum of diagnosed patients. In all of these cancers, the SA concentration was larger than the mean found in the serum of breast cancer patients. Thence, a test value >7 mg/dl, may be indicative and predictive not exclusively of a breast cancer process, but the presence of other possible malignances, that of course merit immediate attention.

The same group also found that rheumatoid arthritis, liver cirrhosis, or severe inflammatory diseases (such as pneumonia) increase the level of SA concentration. Then it is important to remark, that the test is not expected to be conclusive when applied to patients with these conditions present.

It is of note that the inventors have tested women diagnosed with breast cancer, and a control group of healthy females, that as a group have a younger mean age. In the same report of Stefenelli, they find also that the SA expression in the serum increases with age, but in a relatively small percentage, 4-5% and 7%, for the 50-59, and 60-69 groups of age, respectively, when compared to the group of ages 20-49. From 20-49 years the SA concentration remains practically the same. Hence, the increment in the mean that one may calculate for patients of age over 50 years will still fall far below the 7 mg threshold proposed for a negative result, and will be contained within one S.D. of the mean obtained of 3.5±1.0 mg/dl.

In conclusion the inventors have established that SERS on Ag-NPs provides a reliable, easily reproducible, test to measure the concentration of SA dissolved in a fluid. As the SA concentration in the human fluids increase significantly during a malignant process, the same SERS procedure can be used immediately to measure SA levels in women, in particular in the saliva. The inventors have performed a study with 140 breast cancer patients and 104 control individuals. The mean SA concentration in this study for saliva of the control group was 3.5±1.0 mg/dl and that for the breast cancer patients was a mean of 17.0±7.5 mg/dl. The SA test showed a sensitivity of 92%, specificity of 99.8% and a coincident precision of 99.8%. Based on this data it is suggested that an upper limit to consider a deviation of normality a SA concentration above 7 mg/dl in the saliva. Larger SA levels may indicate with high probability the presence of a breast cancer affection, or of other neoplasia, requiring further medical examination and possible treatment. The present SERS test on saliva has the advantages of being non-invasive, highly sensitive, applicable without any age limitations, and of accessible costs.

B. Materials and Methods

Raman and SERS Measurements.

The Raman scattering measurements were done using a HORIBA Explora-One micro Raman spectrometer, using the green laser, 532 nm in wavelength, at an estimated power of 20 mW at the sample. The spectrometer is coupled to an optical microscope Olympus BX41 with a 10× objective. The laser spot is focused to an area of approximately 8-10 μm in diameter. The laser is focused on to the surface of the liquid colloidal solution. The signal is recorded by a cooled CCD at −70° C. The exposure time to record one spectra was set to 10 seconds, for each spectrum four measurements were accumulated. The fluorescence "background" was removed using the Vancouver algorithm (72). The green laser line with a wavelength at 532 nm was used, instead of the more popular 785 nm IR line, as this tended to produce boiling of the liquid solution surface when focused on the liquid samples, severely hindering its application. The spectral range scanned was set from 400 to 1800 cm$^{-1}$.

Sialic Acid and Silver Nanoparticles (AgNPs) Colloidal Solution.

Sialic Acid (SA) is a compound with chemical formula $C_{11}H_{19}NO_9$ and has a molar mass of 309.27 g/mol. In human beings the N-Acetylneuraminic acid (Neu5Ac) form of SA is predominant (1). More relevant for this work, SA normally occupies the terminal, nonreducing positions on cellular membrane glycoproteins. Cancer cells often produce a high density of glycoproteins rich in SA. The cancer cells continuously shed their surface components, that are dragged into the surrounding fluids, a fact that has been recognized, may be used as tumor biological markers present in all human fluids, among them, the saliva (73, 74). Neu5Ac-SA is composed from four recognizable organic units, a chair-like pyranose ring, a carboxyl radical, an acetamide structure, and a glycerol "tail".

The AgNPs were prepared by the standard Turkevich method as described in references (24, 67). To record the SERS, the citrate covered AgNPs in colloidal solutions (2.5×10$^{-3}$ M), 50 μL in volume, are placed in an aluminum container, 100 μL in capacity, either mixed with 25 μL of the sialic acid solution for calibration purposes, as described below, or with the same volume of patient's saliva (2:1 proportion). SEM images indicate that the AgNPs have diameters in the range of 40-50 nm.

Saliva Recollection and Processing.

To each volunteer, an oral cleansing was requested that consisted of two steps, first a vigorous teeth brushing, with disposable tooth brushes that were provided for each patient, followed by two subsequent oral rinses with commercial alcohol-free mouth washer. Afterwards, the patient was instructed to wait several minutes, before depositing 1-1.5 mL of free flowing saliva into a small sterile plastic vial. The saliva recollected was centrifuged for 15 minutes at 6000 rpm. The samples to examine are extracted from the supernatants to determine from them the SA concentration, by comparing with six SA reference concentrations of 1, 5, 10, 15, 20 and 50 mg/dl dissolved in distilled water, measured in the same run, to compensate for any bias introduced by any instrumental day to day variation in performance. The unused sample portions are stored in refrigeration at 4° C.

Subjects.

A total of 246 subjects were included in this study: 106 healthy adult females, who had no recent or actual major illness; and 140 previously diagnosed female patients with breast cancer who attended to oncological medical treatment and follow up supervision in the Civic Hospital of San Luis Potosí, S.L.P. México (Hospital Central or HCSLP). The majority of these women are referred from other city public hospitals when diagnosed as having a breast cancer process in course. The age range of the control group varies from 18-59 years, while that of the breast cancer affected patients, vary between 39-68 years. Inclusion criteria were: no actual and no simultaneous major illness (except breast cancer, for the affected patients), as well as no oral complaints. Exclusion criterion was unwillingness to participate in the study after an oral presentation of the procedure and aims. The study was approved by the HCSLP Ethics Committee. Written informed consent was required from all voluntary participants.

Statistical Analysis.

Statistical analyses of the data were performed using SPSS statistical software (IBM SPSS Statistics version 20 for Windows). Pearson's correlation was performed to establish the degree of correlation between the SA concentrations and the stage of the breast cancer disease. The values are expressed as the mean±standard deviation of the mean. As is standard "P" values at <0.05 were considered statistically significant.

REFERENCES (1) Schauer et al., In *Biology of the Sialic Acids*; ed. A. Rosenberg, pp 7-49. Plenum Press: New York, 1995.
(2) Angata and Varki, *Chem. Rev.* 2002, 102, 439-470.
(3) Sillanaukee et al., *Eur. J. Clin. Invest.* 1999, 29, 413-425.
(4) Crook et al., *Diabetes Care* 2001, 24, 316-322.
(5) Wu et al., *Atherosclerosis* 1999, 145, 261-266.
(6) Öztúrk et al., *Med. Chem.* 2011, 7, 443-447.
(7) Stiles et al., *Annu. Rev. Anal. Chem.* 2008, 1, 601-626.
(8) Ritchie, *Phys. Rev.* 1957, 106, 874-881.
(9) Moskovits, *Chem. Phys.* 1978, 69, 4159-4161.
(10) Loo and Furtak, *Chem. Phys. Lett.* 1980, 71, 68-71.
(11) Campion et al., *J. Am. Chem. Soc.* 1995, 117, 11807-11808.
(12) Fleischmann et al., *J. Chem. Phys. Lett.* 1974, 26, 163-166.
(13) Kneipp et al., *Phys. Rev. Lett.* 1997, 78, 1667-1670.
(14) Nie and Emory, *Science* 1997, 275, 1102-1106.
(15) Lee and Meisel, *Phys. Chem.* 1982, 86, 3391-3395.
(16) Feng et al., *J. Raman Spectrosc.* 2001, 32, 1004-1007.
(17) Meyer and Smith, *Analyst* 2011, 136, 3542-3549.

(18) Cavalu et al., *Biopolymers (Biospectroscopy)* 2001, 62, 341-348.
(19) Munro et al., *Langmuir* 1995, 11, 3712-3720.
(20) Laserna et al., *Anal. Chim. Acta* 1987, 200, 469.
(21) Barthelmes and Plieth, *Electrochim. Acta,* 1995, 40, 2487-2490.
(22) Bell and Sirimuthu, *J. Phys. Chem. A* 2005, 109, 7405-7410.
(23) Lagana et al., *Anal Biochem.* 1993, 215, 266-272.
(24) Turkevich et al., *Discuss Faraday Soc.* 1951, 11, 55-75.
(25) Frisch et al., 2003 GAUSSIAN 03.; Revision B.03. 2003; Gaussian.; Inc.; Wallingford: CT.
(26) Perdew et al., *Phys. Rev. Lett.* 1996, 77, 3865-3868.
(27) Frisch et al., *J. Chem. Phys.* 1984, 80, 3265-3269.
(28) Jiménez-Hoyos et al., *Phys. Chem. Chem. Phys.* 2008, 10, 6621-6629.
(29) Kerker et al., *Appl. Opt.* 1980, 19, 3253-3255.
(30) Melo et al., *J. Raman Spectrosc.* 2011, 42, 644-652.
(31) Schuster et al., *Anal. Chem.* 2000, 72, 5529-5534.
(32) Feofanov et al., *Russian J. Bioorg. Chem.* 1997, 23, 910-918.
(33) Vandenabeele et al., *Anal. Chim. Acta* 2000, 407, 261-274.
(34) Galat, *Acta Biochimica Polonica* 1980, 27, 135-142.
(35) Esmonde-White et al., *Appl. Spectrosc.* 2008, 62, 503-511.
(36) Socrates, *Infrared and Raman Characteristic Group Frequencies,* 3rd ed.; John Wiley & Sons Ltd: Chichester, 2001.
(37) Olivieira et al., *Appl. Spectrosc.* 2002, 56, 306-311.
(38) Harz et al., *Analyst* 2005, 130, 1543-1550.
(39) Rosch et al., *Biopolymers* 2004, 74, 151-156.
(40) Krafft et al., *J. Biomed. Optics* 2012, 17, 040801-15.
(41) Wu et al., *Proc. Natl. Acad. Sci. USA* 2011, 108, 3809-3814.
(42) Schultz and Baranska, *Vibrational Spectroscopy* 2007, 43, 13-25.
(43) Li and Wang, *Vib. Spectrosc.* 2001, 27, 65-74.
(44) Cael et al., *Carbohydr. Res.* 29 (1973) 123-134.
(45) Stewart and Fredericks, *Spectrochim. Acta Part A* 1999, 55, 1615-1640.
(46) Weldon et al., *Appl. Spectrosc.* 1998, 52, 265-269.
(47) Mathlouthi and Koenig, *Adv. Carbohydr. Chem. Biochem.* 1986, 44, 7-89.
(48) Oleinikov et al., in *Spectroscopy of Biological Molecules: Modern Trends,* Carmona P., Navarro R., Hernanz, A. (Eds.), 1997, Kluwer Acad. Publishers, pp. 281-282.
(49) Oleinikov et al., *J. Mol. Struct.* 1999, 480-481, 475-480.
(50) Zhang et al., *Anal. Chem.* 2003, 75, 5703-5709.
(51) Xie et al., *Anal. Biochem.* 2004, 332, 116-121.
(52) Deegan et al., *Nature* 1997, 389, 827-829.
(53) Simakova et al., *Spectroscopy: An International Journal* 2012, 27, 449-453.
(54) Roth et al., *Appl. Spectrosc.* 1993, 47, 1794-1800.
(55) Feofanov et al., *Bioorganicheskaya Khimia* 1996, 22, 706-716.
(56) Feofanov et al., *Bioorganicheskaya Khimia* 1997, 23, 10-918.
(57) Biswas et al., *Chem. Phys. Lett.* 2007, 444, 338-345.
(58) Chowdhury and Ghosh, *Coll. Interf. Sci.* 2004, 277, 121-127.
(59) Mukherjee et al., *Nanotechnology* 2008, 19, 075103-075109.
(60) Wagener et al., *Langmuir* 2012, 28, 6132-6140.
(61) Hilderbrant and Stockburger, *Phys. Chem.* 1994, 88, 5935-5944.
(62) Hull et al., *J. Phys. Chem. A* 2012, 116, 5445-5452.
(63) Redel et al., *Chem. Comm.* 2010, 46, 1159-1161.
(64) Ferlay et al., *Int. J. Cancer.* 2015 136(5):E359-386.
(65) American Cancer Society. Cancer Facts and Figures 2016. Atlanta, Ga.: American Cancer Society; 2016. PDF document available on the world wide web at cancer.org/acs/groups/content/@research/documents/document/acspc-047079.pdf
(66) Bird et al., *Radiology.* 1992, 184(3):613-617.
(67) Vinogradova et al., *Journal of Raman Spectroscopy,* 2014, 45(9):730-735.
(68) Pfaffe et al., *Clinical Chemistry,* 2011, 57(5):675-687.
(69) Liu and Duan, *Oral Oncology,* 2012, 48(7):569-577.
(70) Haynesand and Van Duyne, *Journal of Physical Chemistry B,* 2003, 107(30):668-677.
(71) Han et al., *Analytical and Bioanalytical Chemistry.* 2009, 394(7):1719-1727.
(72) The Vancouver algorithm may be downloaded as a package of free access via the world wide web at fintbox.com/public/project/1956.
(73) Bates, *Ann Intern Med.* 1991, 115:623-638.
(74) Gokmen et al., *Turk J Biochem.* 2004, 29:262-267.
(75) Shinohara et al., *Jpn. J Pharmacol.,* 1994, 64(1):61-63.
(76) Stefenelli et al., *J. Cancer Research Oncology* 1985, 109:55-59.

What is claimed is:

1. A method for identifying a subject with cancer by detecting a N-acetylneuraminic acid analyte in a saliva sample from the subject comprising:
   (a) contacting the sample from a subject suspected of having cancer with a citrate reduced silver nanoparticles forming a N-acetylneuraminic acid silver nanoparticle complex; and
   (b) measuring N-acetylneuraminic acid analyte levels in the sample using label-free detection of the analyte by surface enhanced Raman scattering (SERS) of the N-acetylneuraminic acid/silver nanoparticle complex, wherein an increased level of N-acetylneuraminic acid analyte relative to a control is indicative of the subject having cancer.

2. The method of claim 1, where the cancer is breast cancer.

3. The method of claim 1, wherein a cancer positive sample has a N-acetylneuraminic acid analyte concentration greater than 7 mg/dL.

4. The method of claim 1, wherein the sample volume is less than 20 µL.

5. The method of claim 1, wherein the sample is pretreated before performing steps (a) and (b).

* * * * *